(12) United States Patent
Du et al.

(10) Patent No.: US 11,926,618 B2
(45) Date of Patent: Mar. 12, 2024

(54) HALOGEN-SUBSTITUTED PHENYLATE COMPOUND AND APPLICATIONS THEREOF

(71) Applicant: HINOVA PHARMACEUTICALS INC., Sichuan (CN)

(72) Inventors: Wu Du, Sichuan (CN); Yu Li, Sichuan (CN); Haibo Li, Sichuan (CN); Yuanwei Chen, Sichuan (CN); Chengzhi Zhang, Sichuan (CN); Xinghai Li, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 2 days.

(21) Appl. No.: 17/753,162

(22) PCT Filed: Aug. 20, 2020

(86) PCT No.: PCT/CN2020/110252
§ 371 (c)(1),
(2) Date: Feb. 22, 2022

(87) PCT Pub. No.: WO2021/032161
PCT Pub. Date: Feb. 25, 2021

(65) Prior Publication Data
US 2022/0332707 A1 Oct. 20, 2022

(30) Foreign Application Priority Data
Aug. 21, 2019 (CN) .......................... 201910774991.1

(51) Int. Cl.
| | |
|---|---|
| C07D 403/12 | (2006.01) |
| A61K 31/53 | (2006.01) |
| A61P 1/16 | (2006.01) |
| A61P 3/04 | (2006.01) |
| A61P 3/06 | (2006.01) |
| A61P 3/10 | (2006.01) |
| A61P 5/14 | (2006.01) |
| A61P 5/16 | (2006.01) |
| A61P 9/10 | (2006.01) |
| C07D 253/075 | (2006.01) |

(52) U.S. Cl.
CPC ........ C07D 403/12 (2013.01); C07B 2200/05 (2013.01)

(58) Field of Classification Search
CPC ............. C07D 403/12; C07D 253/075; C07B 2200/05; A61P 3/04; A61P 3/06; A61P 3/10; A61P 5/14; A61P 5/16; A61P 9/10; A61P 1/16; A61K 31/53
See application file for complete search history.

(56) References Cited

FOREIGN PATENT DOCUMENTS

| | | |
|---|---|---|
| CN | 101228135 A | 7/2008 |
| CN | 109574995 A | 4/2019 |
| CN | 110627773 A | 12/2019 |
| CN | 111484481 A1 | 8/2020 |
| WO | 2013045519 A1 | 4/2013 |
| WO | 2019240938 A1 | 12/2019 |
| WO | 2020073974 A1 | 4/2020 |
| WO | 2020169069 A1 | 8/2020 |

OTHER PUBLICATIONS

Taub, R., "Lipid lowering in healthy volunteers treated with multiple doses of MGL-3196, a liver-targeted thyroid hormone receptor-β agonist." Atherosclerosis 230.2 (2013): 373-380.*
Kelly, Martha J. et al.; "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor α Agonist in Clinical Trials for the Treatment of Dyslipidemia"; Journal of Medicinal Chemistry; vol. 57; Apr. 8, 2014;pp. 3912-3923.
Kelly et al. "Discovery of 2-[3, 5-Dichloro-4-(5-isopropyl-6-oxo-1, 6-dihydropyridazin-3-yloxy)phenyl]-3, 6-dioxo-2, 3, 4, 5-tetrahydro[1, 2, 4]triazine-6-carbonitrile (MGL-3196), a Highly Selective Thyroid Hormone Receptor~ Agonist in Clinical Trials for the Treatment of Dyslipidemia"; Journal of Medicinal Chemistry, vol. 57, No. 10, Apr. 8, 2014, ISSN: 0022-2623.

(Continued)

Primary Examiner — John M Mauro
(74) Attorney, Agent, or Firm — NKL Law; Allen Xue

(57) ABSTRACT

A compound of formula (I) or an optical isomer thereof, and pharmaceutically acceptable salts, prodrugs, aquo-complexes or non-aqueous-solvent complexes thereof are provided. Experiments prove that, compared with a control compound MGL-3196, the compound of formula (I), which is obtained through specific substitution sites and specific substitution types, is higher in agonist activity to THR-beta and significantly improved in selectivity on THR-beta/THR-alpha. The compound can be used in preparing THR-beta agonist and drugs for treating adaption diseases (including dyslipidemia, hypercholesteremia, non-alcoholic steatohepatitis and non-alcoholic fatty liver disease) applicable to the THR-beta agonist.

(I)

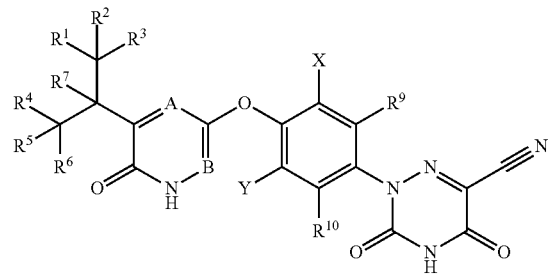

11 Claims, No Drawings

(56) References Cited

OTHER PUBLICATIONS

Scott L. Harbeson et al., "Chapter 24—Deuterium in Drug Discovery and Development", Annual Reports in Medicinal Chemistry, vol. 46, 2011, Available online Oct. 14, 2011, pp. 403-417.
Graham W. Burton, et al., "β-Carotene autoxidation: oxygen copolymerization, non-vitamin A products, and immunological activity", Canadian Journal of Chemistry, Feb. 3, 2014, vol. 92, pp. 305-316.

* cited by examiner

HALOGEN-SUBSTITUTED PHENYLATE COMPOUND AND APPLICATIONS THEREOF

TECHNICAL FIELD

The present invention belongs to the field of pharmaceutical preparation, and particularly relates to a halogen-substituted phenyl ether compound and the use thereof.

BACKGROUND TECHNOLOGY

MGL-3196, a chloride-substituted phenyl ether compound, is a highly selective thyroid hormone receptor β (THR-β) agonist, with an $EC_{50}$ value of 0.21 μM, and its structural formula is

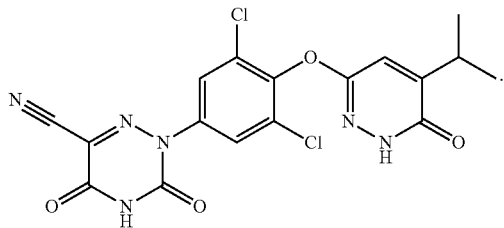 [SMILES: CC(C)c1cc(Oc2c(Cl)cc(-n3nc(C#N)c(=O)[nH]c3=O)cc2Cl)n[nH]c1=O]

Late phase clinical trials are currently underway, showing the therapeutic effect on dyslipidemia, hypercholesterolemia, and nonalcoholic steatohepatitis (NASH). It has been found that the in vivo pharmacokinetic properties and agonistic activity of MGL-3196 as a THR-β agonist need to be improved. Therefore, the structural modification of MGL-3196 and the development of drugs with better properties based on it have become one of the research hotspots. However, chemical modifications would change the structure of the compound to varying degrees, resulting in the difference in both the physical and chemical properties of the compound at various levels, and the impact of these changes on the pharmaceutical properties of the compound is unpredictable. Therefore, how to choose a chemical modification method to obtain a drug with better performances has become one of the most difficult parts in the field.

Deuterium is a common modification method. Deuterated drugs refer to the substitution of some hydrogen atoms in a drug molecule with deuterium. Since the shape and volume of deuterium are close to those of hydrogen in drug molecules, deuterated drugs can generally retain the biological activity and selectivity of the original drug. As the C-D bond is more stable than the C—H bond, the C-D bond of deuterated drugs is less likely to break during the chemical reaction, and thus the half-life may be prolonged.

However, due to the complexity of metabolic processes in biological body, the in vivo pharmacokinetic properties of drugs are influenced by many factors and also correspondingly complex. Changes in the pharmacokinetic properties of deuterated drugs are shown to have obvious contingency and unpredictability compared to the corresponding non-deuterated drugs. Instead of prolonging the half-life, deuteration at some sites may lead to the shortening (Scott L. Harbecon, Roger D. Tung. Deuterium in Drug Discovery and Development, P405-406) and make its pharmacokinetic properties become worse. On the other hand, the hydrogens at certain positions of a drug molecule are not easily deuterated due to steric hindrance and other reasons. Therefore, deuteration of drugs is not arbitrary, and deuterated sites are unpredictable.

In the present invention, it is desirable to obtain a class of drugs with improved activity and pharmacokinetic properties by suitable chemical modification.

CONTENT OF THE INVENTION

The object of the present invention is to provide a class of drugs with high activity, appropriate pharmacokinetic properties, little toxic and side effects and good metabolic stability.

The present invention provides a compound of formula (I) or an optical isomer, a salt, a prodrug, hydrate or a non-aqueous solvate thereof:

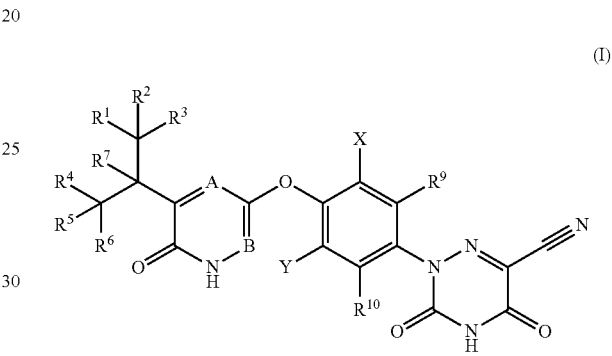

wherein, each of $R^1$-$R^7$, $R^9$, and $R^{10}$ is independently selected from H and D; A and B are each independently selected from the group consisting of N, CH, and CD; X and Y are each independently selected from the group consisting of F, Cl, Br, and I;

in which when B is N, and A is CH or CD, X and Y are not Cl at the same time.

Further, said compound has the structure of formula (II):

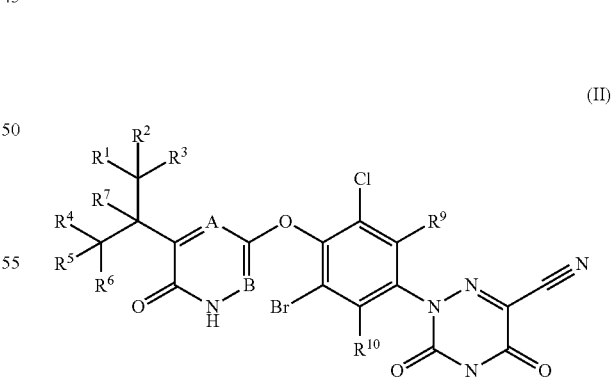

wherein, each of $R^1$-$R^7$, $R^9$, and $R^{10}$ is independently selected from H and D; A and B are each independently selected from the group consisting of N, CH, and CD.

Further, said compound has the structure of formula (III):

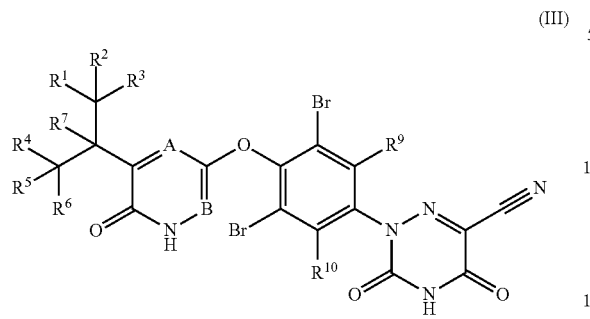

(III)

wherein, each of $R^1$-$R^7$, $R^9$, and $R^{10}$ is independently selected from H and D; A and B are each independently selected from the group consisting of N, CH, and CD.

Further, said compound has the structure of formula (IV):

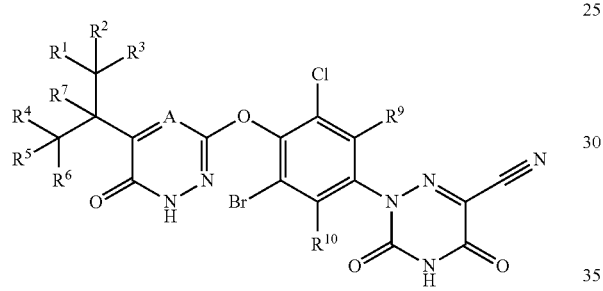

(IV)

wherein, each of $R^1$-$R^7$, $R^9$, and $R^{10}$ is independently selected from H and D; A is selected from the group consisting of N, CH, and CD;

preferably, $R^7$, $R^9$, and $R^{10}$ are each independently selected from H; each of $R^1$-$R^6$ is independently selected from H and D; A is selected from CH and CD.

Further, said compound has the structure of formula (V):

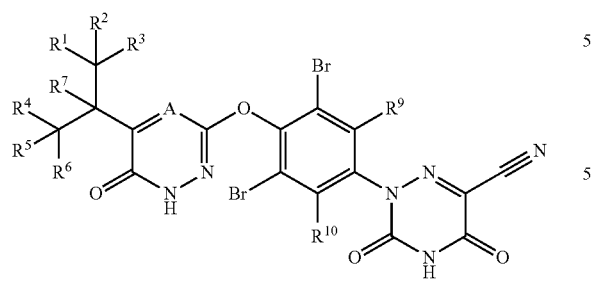

(V)

wherein, each of $R^1$-$R^7$, $R^9$, and $R^{10}$ is independently selected from H and D; A is selected from the group consisting of N, CH, and CD;

preferably, $R^7$, $R^9$, and $R^{10}$ are each independently selected from H; each of $R^1$-$R^6$ is independently selected from H and D; A is selected from CH and CD.

Further, said compound has the structure of formula (VI):

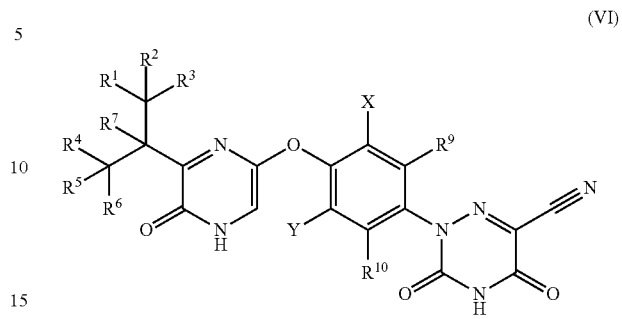

(VI)

wherein, each of and $R^1$-$R^7$, $R^9$, and $R^{10}$ is independently selected from H and D; X and Y are each independently selected from the group consisting of F, Cl, Br, and I; preferably, X and Y are each independently selected from the group consisting of Cl and Br.

Further, said compound is selected from the group consisting of the following compounds:

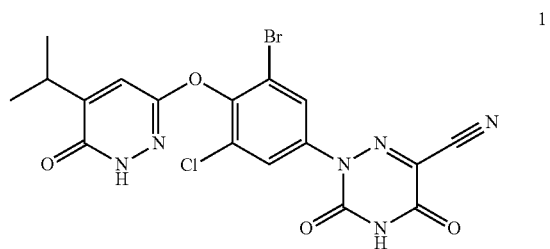

1

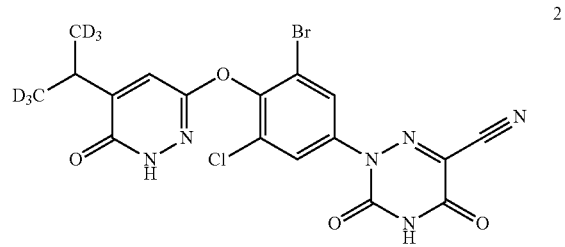

2

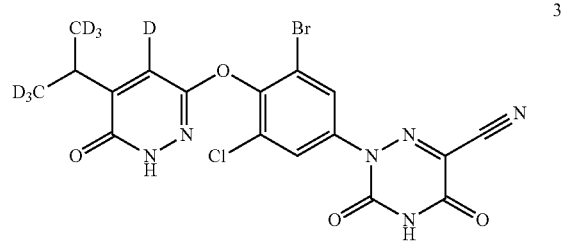

3

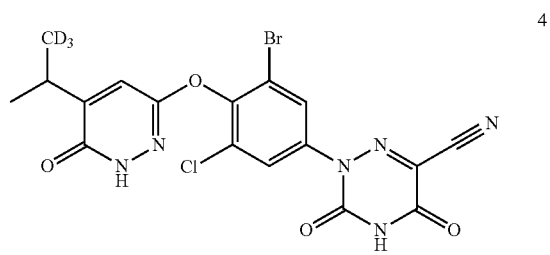

4

5
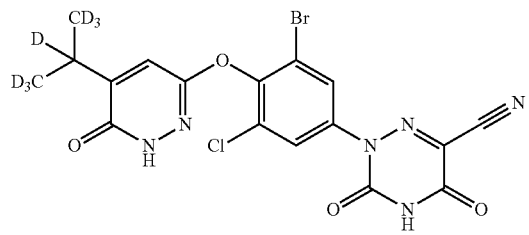
6
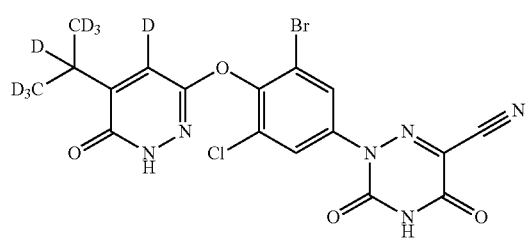
7
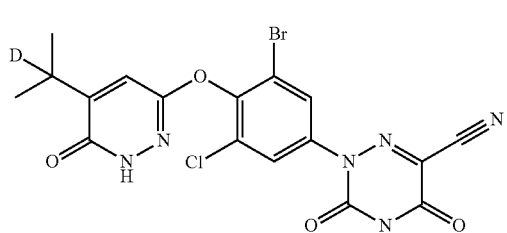
8
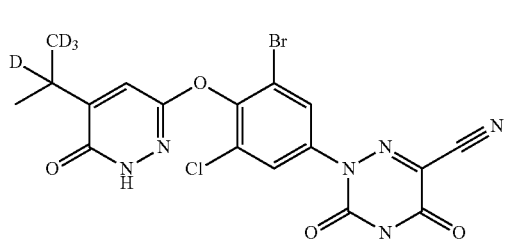
9
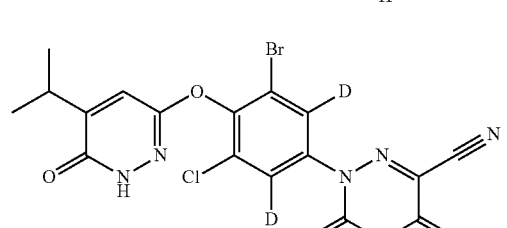
10
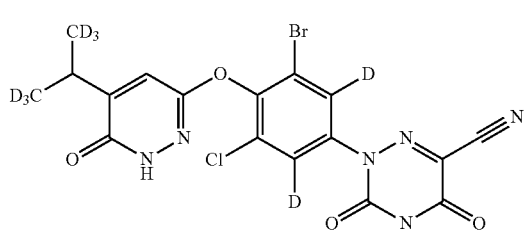
11
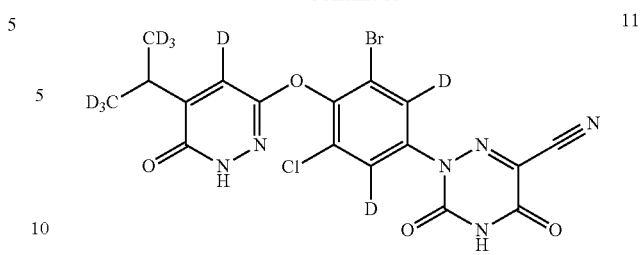
12
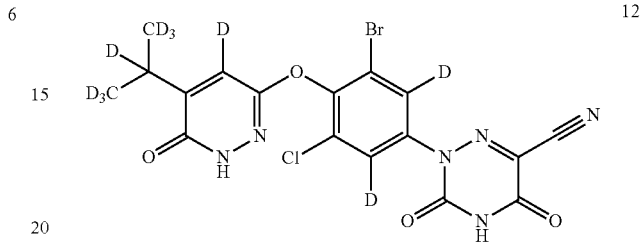
13
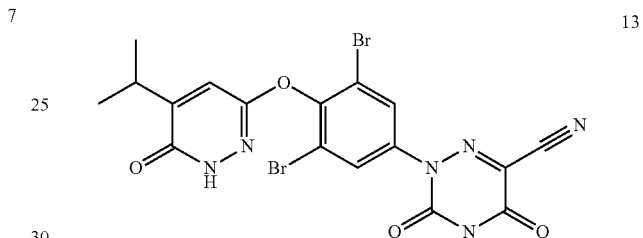
14
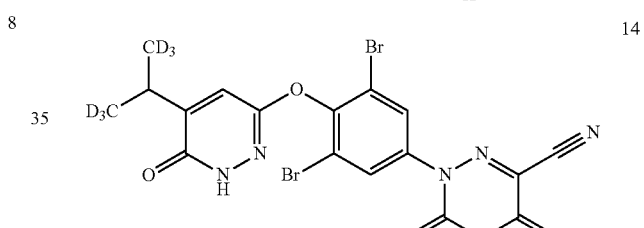
15
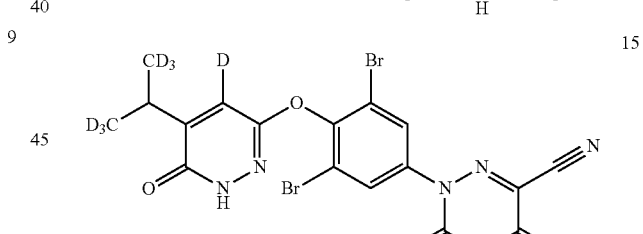
16
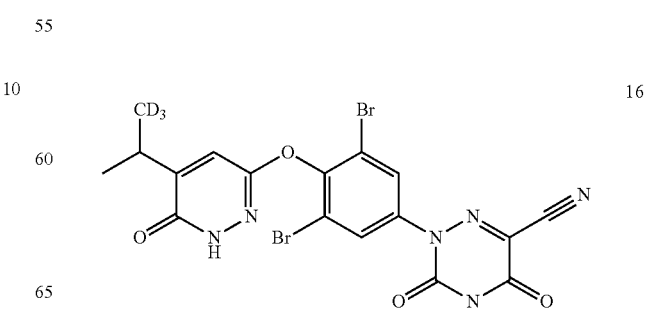

-continued
17
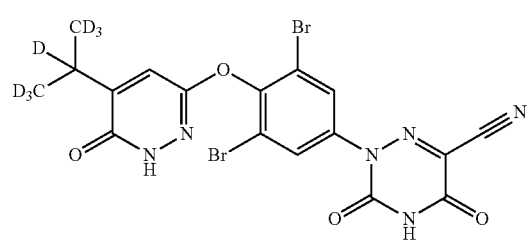
18
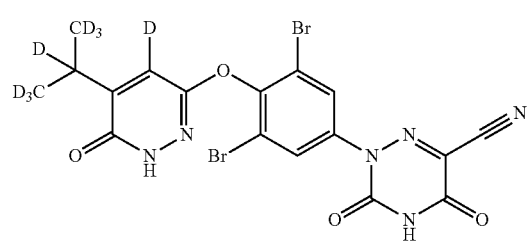
19
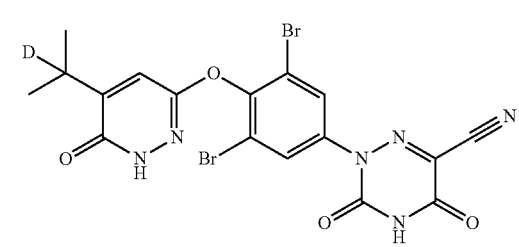
20
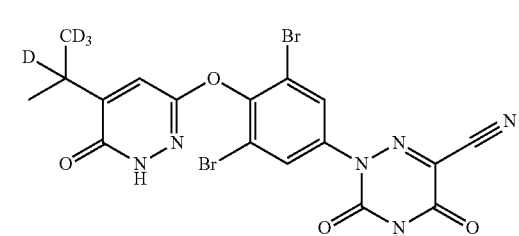
21
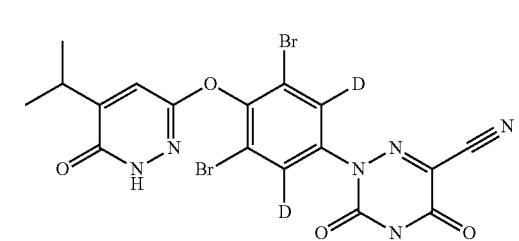
22
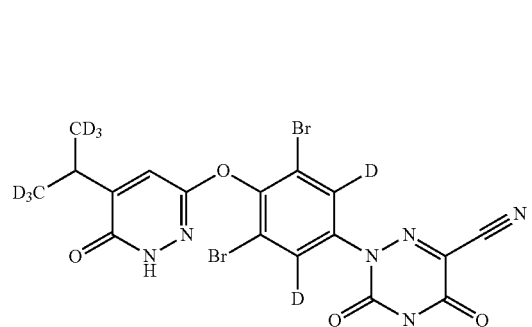
-continued
23-1
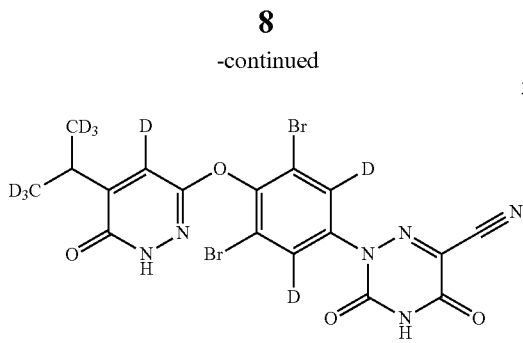
23-2
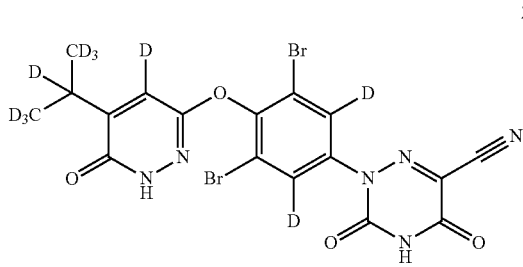
24
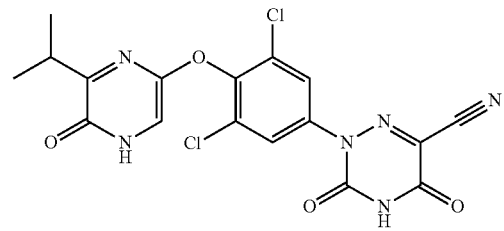
25
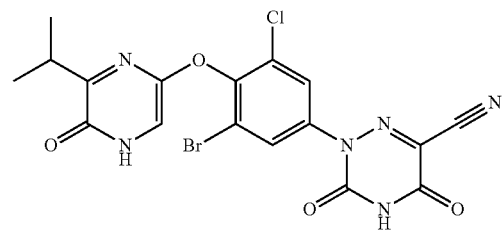
26
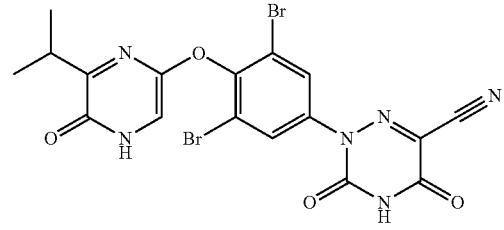
27
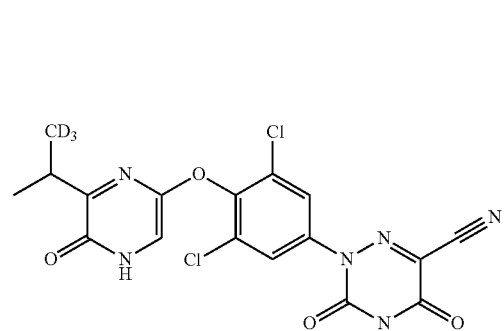

-continued
28
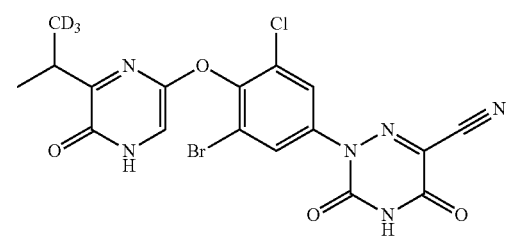
29
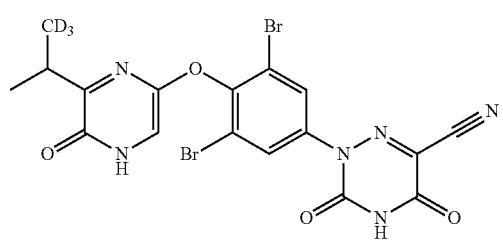
30
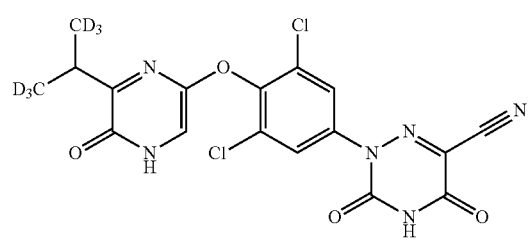
31
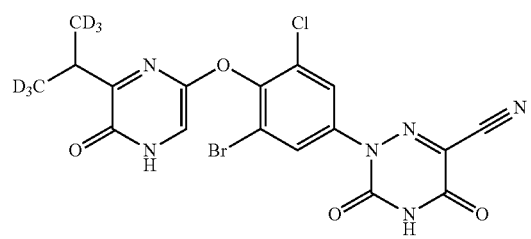
32
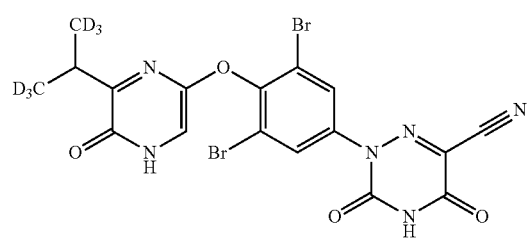
33
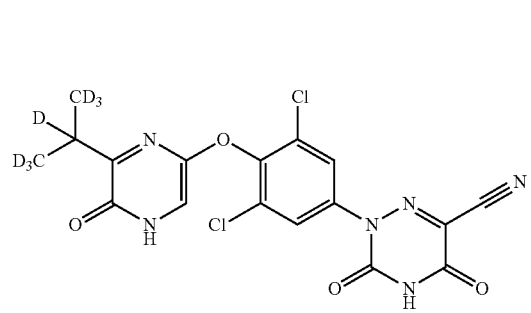
-continued
34
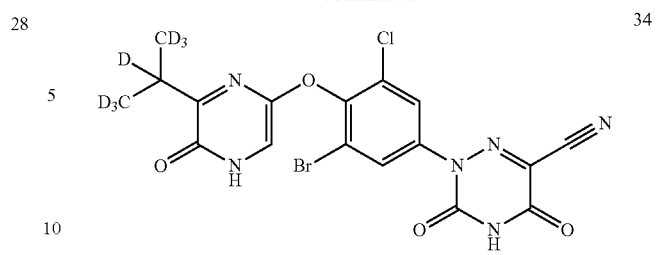
35
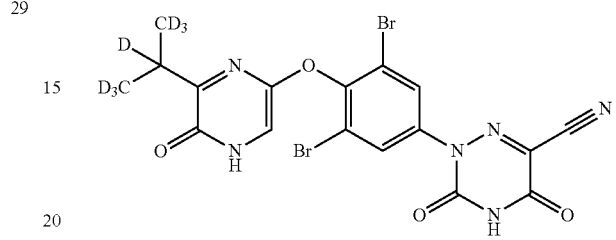
36
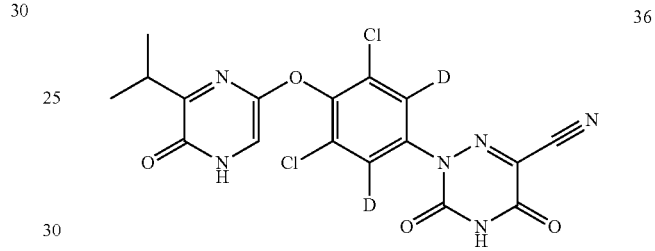
37
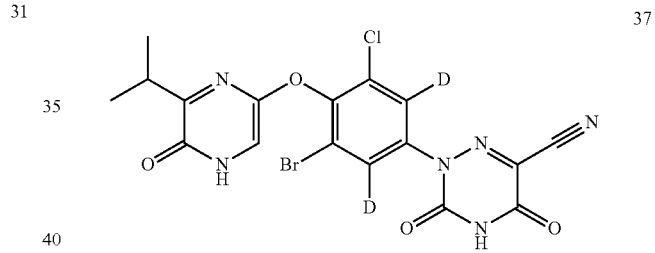
38
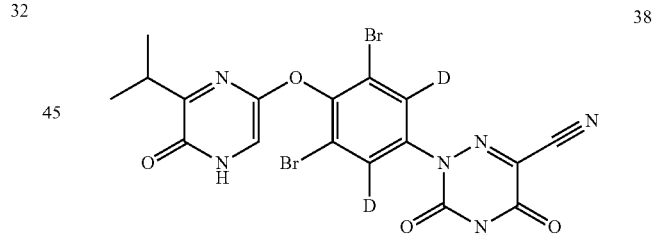
39
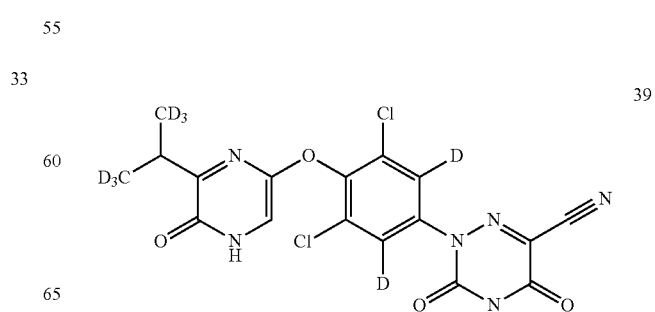

40

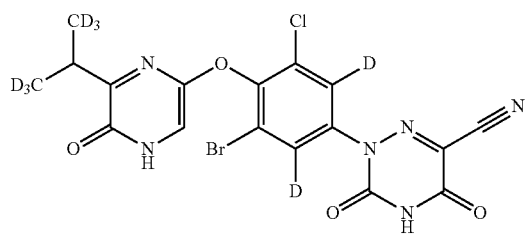

41

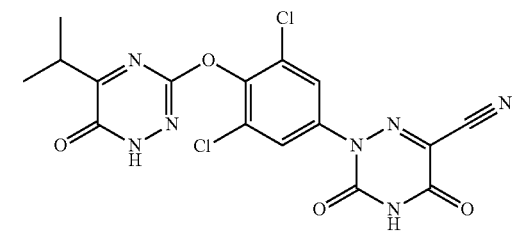

42

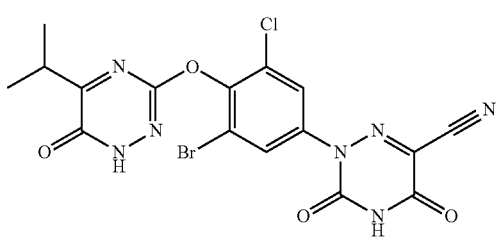

43

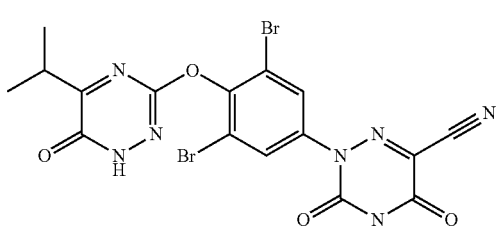

44

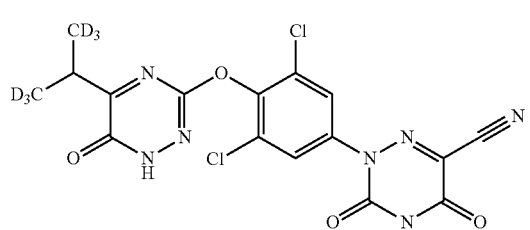

45

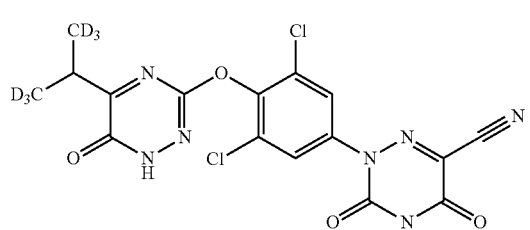

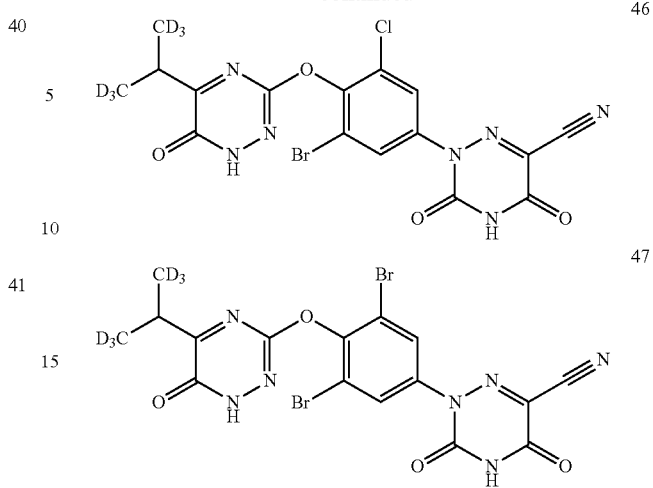

The present invention also provides the use of the compound mentioned above or an optical isomer, a salt, a prodrug, a hydrate or a non-aqueous solvate thereof in the preparation of THR-β agonists.

Further, said THR-β agonist is a drug for lowering cholesterol and treating dyslipidemia and nonalcoholic fatty liver disease.

Further, said THR-β agonist is a drug for the treatment of familial hypercholesterolemia and non-alcoholic steatohepatitis.

The present invention also provides the use of the compound mentioned above or an optical isomer, a salt, a prodrug, a hydrate or a non-aqueous solvate thereof in the preparation of THR-α agonists; preferably, said THR-α agonist is a drug for the treatment of diffuse toxic goiter.

The present invention also provides a medicament for lowering cholesterol and treating dyslipidemia and nonalcoholic fatty liver disease, which is a preparation containing an active ingredient that is the compound mentioned above or an optical isomer, a salt, a prodrug, a hydrate or a non-aqueous solvate thereof, and pharmaceutically acceptable auxiliary materials.

As used herein, "deuteration" refers to the substitution of one or more hydrogens in a compound or group with deuterium. Deuterium can be monosubstituted, disubstituted, polysubstituted, or fully substituted. In another preferred example, the content of deuterium isotope at the substitution position is greater than the natural content (0.015%), preferably greater than 50%, more preferably greater than 75%, more preferably greater than 95%, more preferably greater than 97%, more preferably greater than 99%, and more preferably greater than 99.5%.

As used herein, the term "compound of the present invention" refers to a compound of formula (I). The term also includes various optical isomers, salts, prodrugs, hydrates, or non-aqueous solvates of the compound of formula (I).

The active ingredient mentioned herein refers to any substance or mixture used in the manufacture of medicaments, which has pharmacological activity or other direct effects in the diagnosis, treatment, symptom relief, treatment or prevention of diseases or can affect the function or structure of the body.

The pharmaceutically acceptable excipient has a certain physiological activity, but the addition of the excipient cannot change the dominant position of the pharmaceutical composition in the treatment process of a disease, but only play auxiliary roles. These auxiliary effects are only the use of the known activity of the excipient and are the usual auxiliary treatment methods in the field of medicine. If the auxiliary ingredient is used in combination with the pharmaceutical composition of the present invention, it is still in the protection scope of the present invention.

"A non-aqueous solvate" means a solvate other than a hydrate.

It has been confirmed that compared with the control compound MGL-3196, the compound of formula (I), which is obtained by specific substitution sites and specific substitution types in the present invention, displays a higher agonistic activity on both THR-β and THR-α, and especially for THR-β, the compound of the present invention has a significantly improved agonistic activity and selectivity. In addition, the compound of the present invention also demonstrates a significantly improved pharmacokinetic properties, and has a good application prospect in the preparation of THR-β agonists and drugs for the treatment of THR-β agonist indications (including dyslipidemia, hypercholesteremia, non-alcoholic steatohepatitis (NASH) and non-alcoholic fatty liver disease (NAFLD)).

Obviously, based on the above content of the present invention, according to the common technical knowledge and the conventional means in the field, without department from the above basic technical spirits, other various modifications, alternations, or changes can further be made.

By following specific examples of said embodiments, the above content of the present invention is further illustrated. But it should not be construed that the scope of the above subject matter of the present invention is limited to the following examples. The techniques realized based on the above content of the present invention are all within the scope of the present invention.

EXAMPLES

The starting materials and instruments used in the present invention are all known articles, which are commercially available.

Example 1 Synthesis of Compound 2

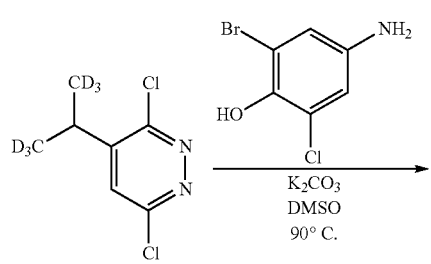

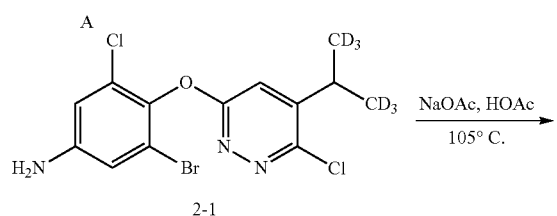

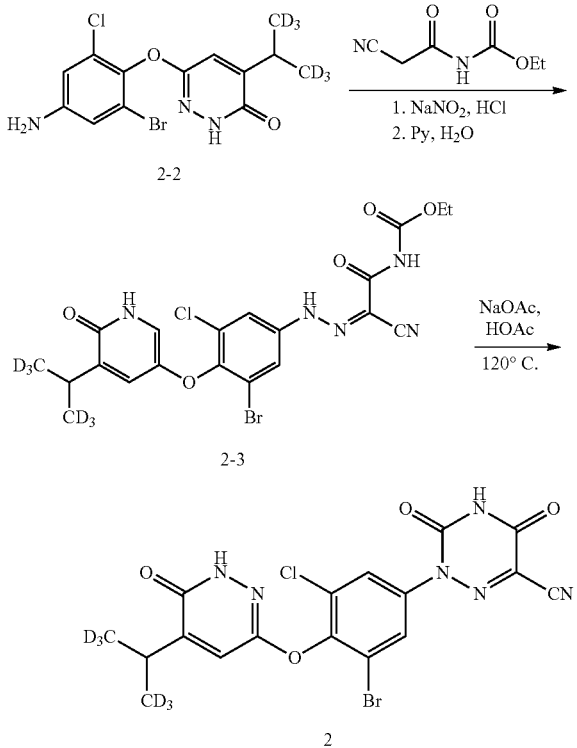

(1) Synthesis of compound 3-bromo-5-chloro-44(6-chloro-5-di(trideuteromethyl) methylpyridazin-3-yl)oxy)aniline (compound 24)

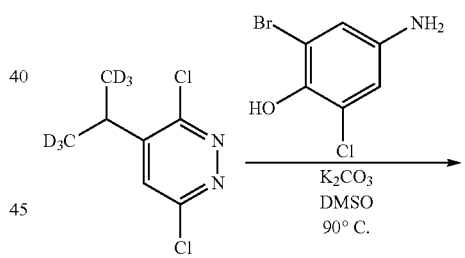

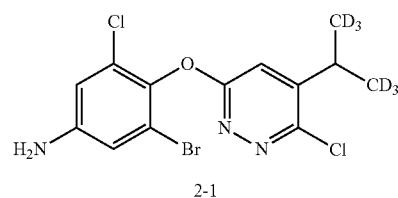

Synthesis of 3,6-dichloro-4-(1,1,1,3,3,3-hexadeuteropropyl-2-yl)pyridazine (compound A):

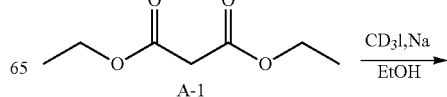

-continued

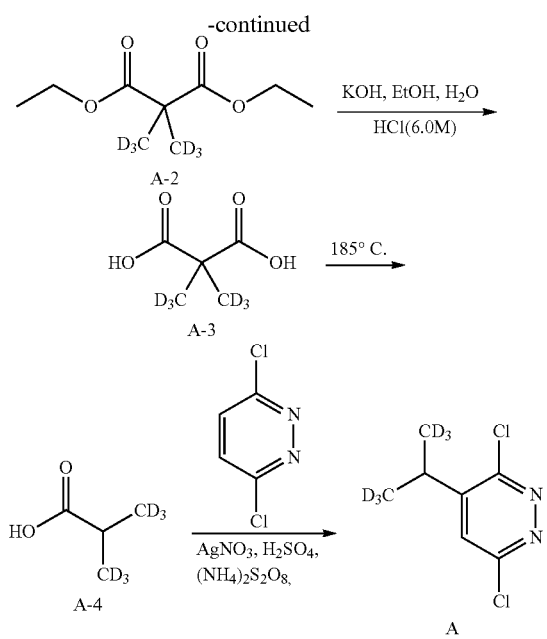

Using the method in literature (Canadian Journal of Chemistry, 2014, 92, 305), 2-trideuteromethyl-3,3,3-trideuteropropionic acid A-4 was prepared. 2-Trideuteromethyl-3,3,3-trideuteropropionic acid (1.4 g, 15 mmol) was weighed and placed in a 100 mL three-necked round bottom flask, to which was added 20 mL of water, and then the solution was stirred at room temperature till the solution became clear. Then, 3,6-dichloropytidazine (2.2 g, 15 mmol) was added to the system, and the solution was further stirred at room temperature. Then, silver nitrate (2.5 g, 15 mmol) was added to the system, and then the system was moved into an oil bath for heating, and allowed to react under stirring. When the internal temperature of the system rose to 50° C., concentrated sulfuric acid (3.5 mL) was added dropwise to the system, and after addition, the system was further stirred for 10 min at this temperature. Then, when the internal temperature of the system rose to 60° C., 6 mL aqueous solution of ammonium persulfate (10.3 g, 45 mmol) was added dropwise to the system. When the internal temperature of the system rose to 70° C., the mixture was allowed to react for additional 30 min under stirring at this temperature. Heating was stopped, and the system was naturally cooled to room temperature. Then, the system was transferred to an ice water bath for cooling under stirring, and after 15 min, NaOH solution (6.0 M) was drop added to the system to adjust pH value of the system to be about 8. Ethyl acetate (20 mL) was added to the system, and the solution was stirred vigorously, followed by standing for separation of layers. The aqueous phase was extracted with ethyl acetate (10 mL×3). The organic phase was combined, sequentially washed with water (10 mL×3) and saturated saline (20 mL), and dried over anhydrous sodium sulfate. The solution was concentrated under reduced pressure to obtain the crude product, which was separated and purified by column chromatography, to provide 3,6-dichloro-4-(1,1,1,3,3,3-hexadeuteropropyl-2-yl) pyridazine (compound A, 1.7 g) as an off-white solid, with a yield of 58%. MS (ESI) m/z 197.2 [M+H]⁺. ¹H NMR (400 DMSO-d₆) δ7.98 (d, J=0.8 Hz, 1H), 3.12 (s, 1H).

3-Bromo-5-chloro-4-di(trideuteromethyl)methylpyridazine (A, 450 mg, 2.28 mmol) was weighed and placed in a 100 mL three-necked round bottom flask, to which was added 10 mL of dimethylsulfoxide, and the solution was stirred at room temperature till it became clear. The system was purged with argon, and this operation was repeated ten times to ensure the inert gas atmosphere in the system. Subsequently, 4-amino-2-bromo-6-chlorophenol (508.0 mg, 2.28 mmol) and anhydrous potassium carbonate (1.3 g, 9.12 mmol) were successively added to the system. After addition, the system was moved in an oil bath at 90° C., heated and reacted overnight under stirring. After 24 h, the starting material disappeared by detection. Heating was stopped, and the system was allowed to naturally cool to room temperature. Ethyl acetate (20 mL) and water (20 mL) were added to the system and stirred vigorously, followed by standing for separation of layers. The aqueous phase was extracted with ethyl acetate (20 mL×3). The organic phase was combined, sequentially washed with water (10 mL×3) and saturated saline (20 mL), and dried over anhydrous sodium sulfate. The solution was concentrated under reduced pressure to remove the solvent and obtain the crude product, which was separated by column chromatography, to provide 3-bromo-5-chloro-4-((6-chloro-5-di(trideuteromethyl)methylpyridazine-3-yl)oxy)aniline as light yellowish-brown solid (2-1, 463.0 mg), with a yield of 52.9%. MS (ESI) m/z 382.0 [M+H]⁺.

(2) Synthesis of compound 6-(4-amino-2-bromo-6-chlorophenoxy)-4-di(trideuteromethy) methylpyridazine-3(2H)-one (compound 2-2)

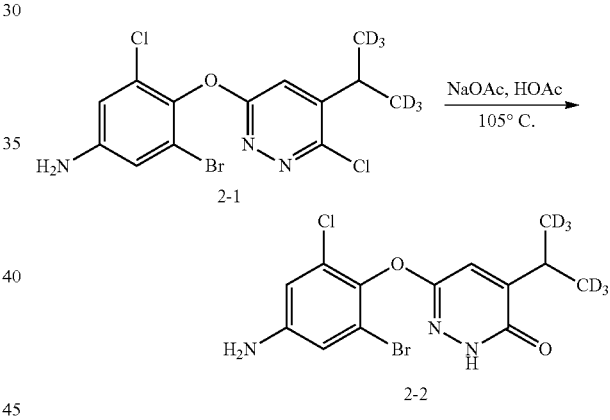

3-Bromo-5-chloro-4-((6-chloro-5-di(trideuteromethypmethylpyridazine-3-yl)oxy) aniline (341.0 mg, 0.89 mmol) was weighed and placed in a 50 mL three-necked round bottom flask, to which was added glacial acetic acid (10 mL), and then the mixture was stirred at room temperature. Subsequently, anhydrous sodium acetate (256.0 mg, 3.12 mmol) was added to the system. After addition, the system was transferred in an oil bath at 105° C., and allowed to stir and react under reflux. After 24 h, the heating was stopped, and the system was naturally cooled to room temperature. The solvent was removed by rotatory evaporation, and water (50 mL) was added to the system, which was then transferred in an ice-water bath for cooling under stirring. When the internal temperature of the system was reduced to 5° C., sodium hydroxide solution (1.0 M) was added dropwise to the system, and pH value of the system was adjusted to be about 9. After that, ethyl acetate (30 mL) was added to the system and vigorously stirred, followed by standing for separation of layers. The aqueous phase was extracted with ethyl acetate (25 mL×2). The organic phase was combined, sequentially washed once with water (20 mL) and saturated saline (20 mL), and dried over anhydrous sodium sulfate. The solution was concentrated under reduced pressure to provide pale yellow solid. Methanol (10 mL) and NaOH solution (1.0 M, 10 mL) were sequentially added to a 100 mL three-necked round bottom flask containing the solid, and after addition, the system was moved in an oil bath at 105° C. for reaction under reflux. After 16 h, heating was stopped, the oil bath was removed, and the system was warmed to room temperature. The solvent was removed by rotatory evaporation, and ethyl acetate (60 mL) and water (40 mL) were added to the residue. The resultant solution was vigorously stirred, and then allowed to stand for separation of layers. The aqueous layer was extracted with ethyl acetate (25 mL*2). The organic layer was combined, sequentially washed with water (20 mL*2) and saturated saline (20 mL), and dried over anhydrous sodium sulfate. The solvent was removed by rotatory evaporation to provide the crude product, which was separated by column chromatography to obtain 6-(4-amino-2-bromo-6-chlorophenoxy)-4-di(trideuteromethyl)methylpyridazine-3(2H)-one as pale yellow solid (2-2, 200.0 mg), with a yield of 61.5%. MS (ESI) m/z 364.2 [M+H]$^+$. $^1$H NMR (400 MHz, DMSO-d$_6$) δ12.13 (s, 1H), 7.26 (s, 1H), 6.82(d, J=4.0 Hz, 1H), 6.70 (d, J=4.0 Hz, 1H), 5.60 (s, 2H), 2.99 (s, 1H).

(3) Synthesis of ethyl (2-cyano-2-(2-(3-bromo-5-chloro-4-((5-di(trideuteromethyl) methyl-6-oxo-1,6-dihydropyridazine-3-yl)oxy)phenyl)hydrazono)acetyl)carbamate (compound 2-3)

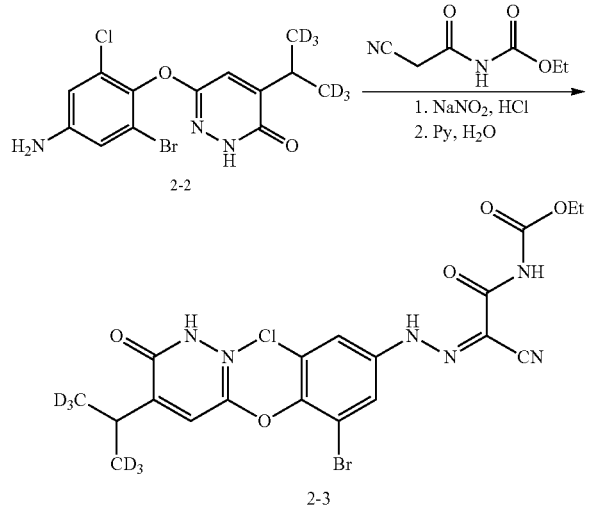

6-(4-Amino-2-bromo-6-chlorophenoxy)-4-di(trideuteromethyl)methylpyridazine-3 (2H)-one (153 mg, 0.42 mmol) was weighed and placed in a 50 mL three-necked round bottom flask, to which was added water (5.6 mL), and the solution was stirred at room temperature. Subsequently, concentrated hydrochloric acid (2.8 mL) was added to the system. After addition, the system was transferred in an ice water bath for cooling under stilling. When the internal temperature of the system was reduced to 0° C., 0.4 mL aqueous solution of sodium nitrite (36.5 mg, 0.53 mmol) was added dropwise to the system. After adding, the system was further stirred and reacted for 30 min at this temperature, N-cyanoacetylurea (72.0 mg, 0.46 mmol) was weighed and placed in a 25 mL single-necked round bottom flask, to which were added water (9.4 mL) and pyridine (2.8 mL). The resultant mixture was stirred at room temperature to obtain a clear solution, and then the system was transferred to an ice water bath to cool under stirring for additional 30 min. The diazotizing reaction solution was added slowly to the system containing N-cyanoacetylurea, and the dropping rate was controlled so that the internal temperature of the system did not exceed 5° C. After addition, the system was allowed to stir and react in the ice water bath at this temperature. After 1 h, the reaction was completed by TLC detection. The system was filtered by suction, and the filter cake was rinsed several times with a small amount of water, washed several times with n-hexane, and dried to obtain ethyl (2-cyano-2-(2-(3-bromo-5-chloro-4-((5-di(trideuteromethyl)methyl-6-oxo-1,6-dihydropyridazin-3-yl) oxy)phenyl)hydrazono)acetyl)carbamate as orange-red solid (2-3, 153.0 mg), with a yield of 68.6%, which was directly used in the next step without further purification. MS (ESI) m/z 531.1 [M+H]$^+$.

(4) Synthesis of compound 2-(3-bromo-5-chloro-4-((5-dideuteromethylmethyl-6-oxo-1,6-dihydropyridazin-3-yl) oxy)phenyl)-3,5-dioxo-2,3,4,5-tetrahydro-1,2,4-triazine-6-nitrile (compound 2)

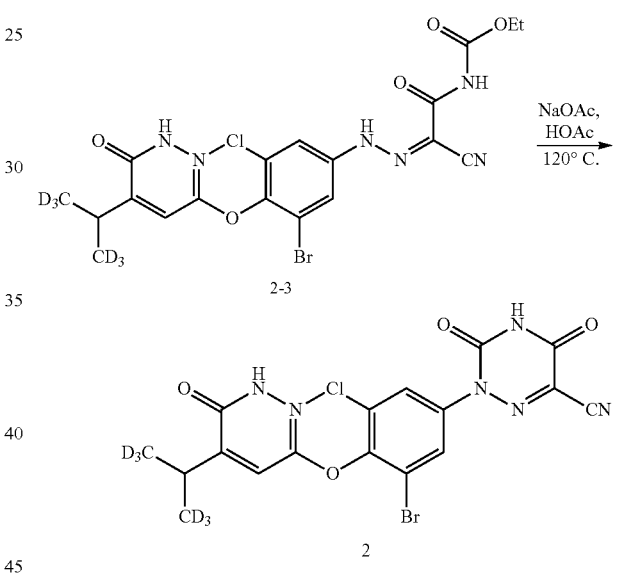

Ethyl (2-cyano-2-(2-(3-bromo-5-chloro-4-((5-di(trideuteromethyl)methyl-6-oxo-1,6-dihydropyridazine-3-yl)oxy) phenyl)hydrazono)acetyl)carbamate (153 mg, 0.29 mmol) was weighed and placed in a 25 mL single-necked round bottom flask, to which was added glacial acetic acid (5 mL), and then the mixture was stirred at room temperature. Subsequently, anhydrous sodium acetate (118.0 mg, 1.44 mmol) was added to the system. After addition, the system was transferred in an oil bath at 120° C., and allowed to stir and react under heating. After 1.5 h, the starting material was completely consumed by TLC detection. The heating was stopped, and the system was naturally cooled to room temperature. The system was then transferred in an ice-water bath for cooling under stirring. When the internal temperature of the system was reduced to 5° C., to which was added ice water, and the resultant solution was vigorously stirred for 20 min. Then, the solution was filtered by suction, and the filter cake was rinsed with water for several times, which was then dissolved in ethyl acetate, dried over anhydrous sodium sulfate. The solvent was removed by rotatory evaporation to obtain a crude product, which was separated and purified by Pre-TLC to obtain 2-(3-bromo-5-chloro-4-((5-di(trideuteromethyl)methyl-6-oxo-1,6-dihydropyridazine-3-yl)oxy)phenyl)-3,5-dioxo-2,3,4,5-tetrahydro-1,2,4-triazine-6-nitrile as light orange solid (compound 2, 54.0 mg), with a yield of 38.6%. MS (ESI) m/z 485.0 [M+H]⁺. ¹H NMR (400 MHz, DMSO-d₆) δ13.29 (s, 1H), 12.24 (s, 1H), 7.90 (d, J=4.0 Hz, 1H), 7.82 (d, J=4.0 Hz, 1H), 7.45 (s, 1H), 3.02 (s, 1H).

Example 2 2-(3-bromo-5-chloro-4-((4-deutero-5-(1,1,1,3,3,3-hexadeuteropropyl-2-yl)-6-oxo-1,6-dihydropyrazin-3-yl)oxy)phenyl)-3,5-dioxy-2,3,4,5-tetrahydro-1,2,4-triazine-6-nitrile (compound 3)

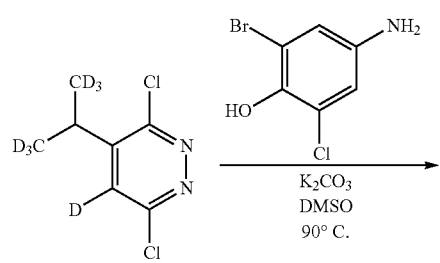

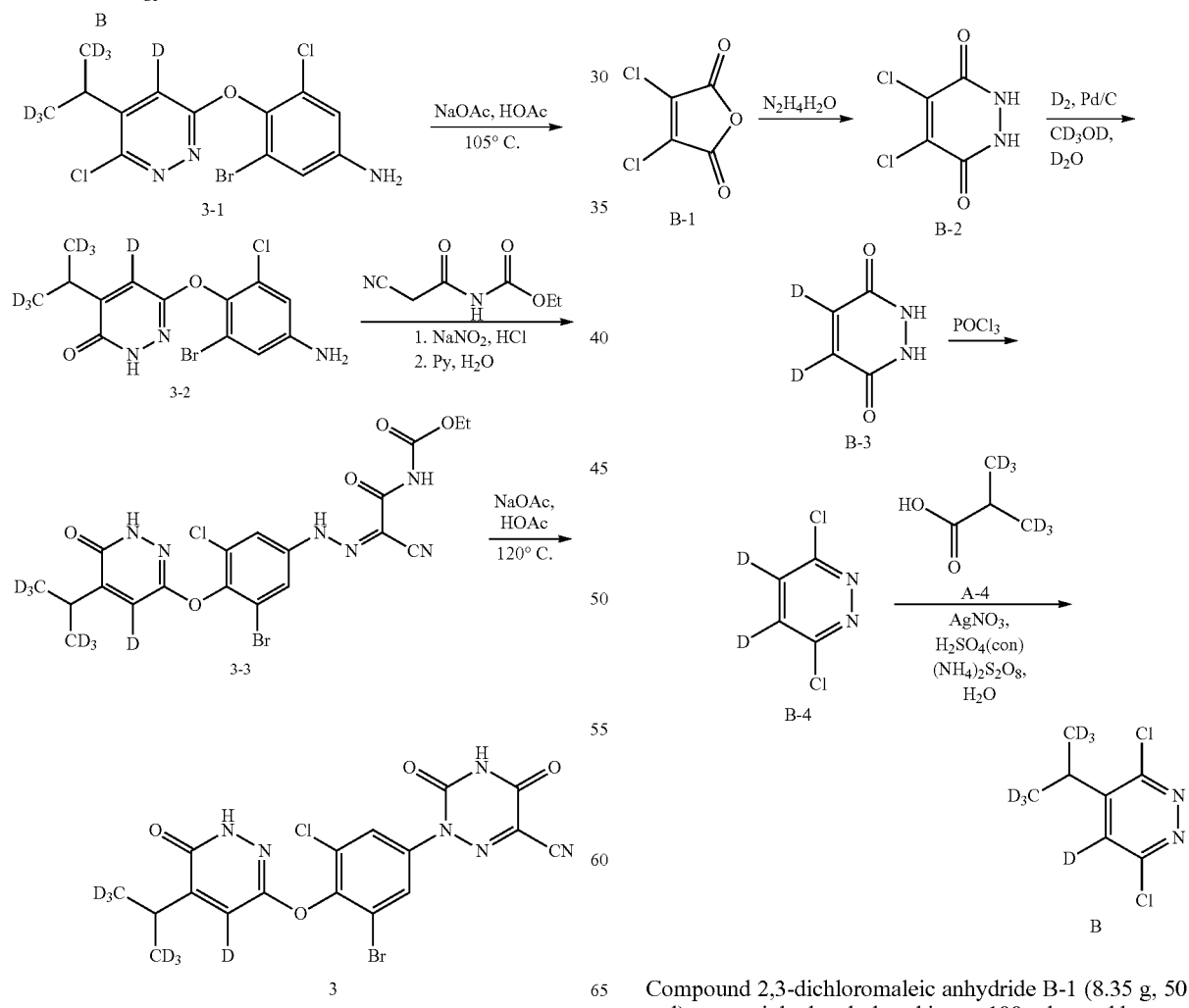

(1) Synthesis of compound 3-bromo-5-chloro-4-((6-chloro-5-(propan-2-yl-1,1,1,3,3,3-hexadeutero)pyrazin-3-yl-4-deutero)oxy)aniline

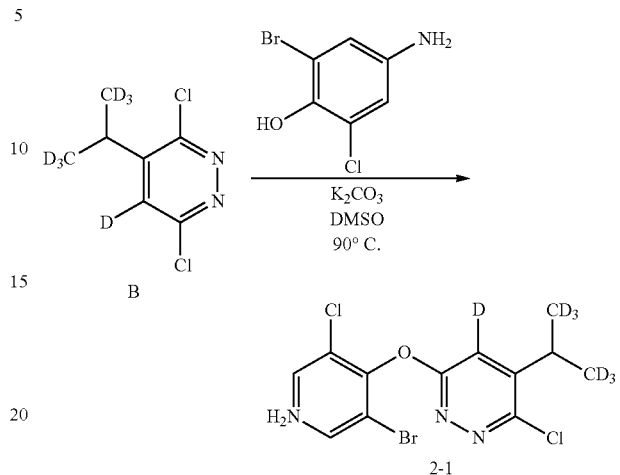

Synthesis of 3,6-dichloro-4-deutero-5-(1,1,1,3,3,3-hexadeuteropropyl-2-yl) pyridazine (compound B):

Compound 2,3-dichloromaleic anhydride B-1 (8.35 g, 50 mmol) was weighed and placed into a 100 ml round bottom flask, to which were successively added 40 ml of water and hydrazine hydrate (2.5 g, 50 mmol), and then the reaction solution was heated to reflux and allowed to react for 4 h under reflux. Then, the reaction mixture was cooled to room temperature, and kept in an ice water bath for 30 min. The reaction solution was filtered, and the filter cake was rinsed with 100 ml of water and dried to obtain 4,5-dichloromaleic hydrazide (B-2, 5.0 g), with a yield of 55.3%, MS (ESI) m/z 181.0 [M+H]$^+$.

Synthesis of 4,5-dideuteromaleic hydrazide (B-3): Method 1: 4,5-dichloromaleic hydrazide (2.0 g, 11.05 mmol) was weighed and placed into a 100 ml single-necked round bottom flask, to which were successively added 50 ml of methanol-d$_4$, 10 ml of deuterated water, and 200 mg of Pd/C. The system was purged with deuterium for 3 times, and then the mixture was allowed to react at room temperature for 40 h. After that, the reaction solution was filtered, and the filtrate was concentrated under reduced pressure to dry. The residue was beaten in 6 ml of methanol, and then filtered. The filtrate was dried to provide compound 4,5-dideuteromaleic hydrazide (1.0 g), with a yield of 79%, MS (ESI) m/z 115.2 [M+H]$^+$. $^{13}$C NMR (101 MHz, DMSO-d$_6$) δ156.76, 130.50. Method 2: maleic hydrazide (5.6 g, 50 mmol) was added to a round bottom flask, to which were successively added 80 ml of deuterated water and 500 mg of Pd/C. The system was purged with hydrogen three times, and then the mixture was heated and refluxed for 72 h in hydrogen atmosphere. The reaction solution was cooled to room temperature and filtered. The filter cake was added to a round bottom flask, and the above procedure was repeated. After the reaction was completed, 100 ml of methanol was added to the filter cake, and then the resultant solution was refluxed for 30 min. Then, the solution was filtered, and the filtrate was concentrated under reduced pressure to dry, to provide 2.5 g of 4,5-dideuteromaleic hydrazide, with a yield of 43.87%.

Synthesis of 4,5-dideutero-3,6-dichloropyridazine (B-4)

4,5-Dideuteromaleic hydrazide (1.0 g, 8.74 mmol) was weighed and placed in a 100 ml round bottom flask, to which was added 15 ml of phosphorus oxychloride, and then the solution was refluxed at 115° C. for 4 h. The solution was concentrated under reduced pressure to dry, and then cooled in an ice water bath, to which was added 20 ml of ice water. The resultant solution was adjusted to be pH=9.0 with ammonia water, and then 30 ml of dichloromethane was added for extraction. The water layer was further extracted once with 20 ml of dichloromethane. The organic layer was combined, sequentially washed with water and saturated saline, and dried over anhydrous sodium sulfate. The solution was concentrated under reduced pressure to dry, to provide 1.2 g of compound 4,5-dideutero-3,6-dichloropyridazine, with a yield of 90.9%. $^{13}$C, NMR (101 MHz, DMSO-d$_6$) δ156.3, 131.9 (t, J=27 Hz). MS (ESI) m/z 151 [M+H]$^+$.

Compound 3,6-dichloro-4,5-dideuteropyridazine B-4 (604 mg, 4.0 mmol) was added into 10 ml of water, to which was added compound A-4 (372 mg, 4.0 mmol), and then AgNO$_3$ (680 mg, 4 mmol) was added to the system under stirring. When the temperature rose to 50° C., concentrated sulfuric acid (1 mL) was slowly added dropwise to the system. After addition, the system was heated to 60° C. and allowed to react for 10 min at this temperature. Ammonium persulfate (2.74 g, 12 mmol) was dissolved in 6 mL of water and then added dropwise to the system. After addition, the system was heated to 70° C. and allowed to react for additional 30 min at this temperature. The reaction was detected by TLC, and when the starting material disappeared, heating was stopped. The system was transferred to an ice water bath for cooling. The resultant solution was adjusted to be pH=8.0 with 6 N of NaOH aqueous solution, and extracted with ethyl acetate (30 mL). The organic layer was sequentially washed with water and saturated saline, dried over anhydrous sodium sulfate, and then concentrated under reduced pressure to dry. The residue was separated and purified by column chromatography (petroleum ether/ethyl acetate=10:1), to provide compound B (500 mg), with a yield of 63.1%, MS (EST) m/z 198.1 [M+H]$^+$.

3,6-Dichloro-4-di(trideuteromethyl)methyl-5-deuteropyridazine B (285.0 mg, 1.44 mmol) was weighed and placed in a 25 mL single-necked round bottom flask, to which was added 8 mL of dimethylsulfoxide, and the solution was stirred at room temperature till it became clear. Subsequently, 4-amino-2-bromo-6-chlorophenol (320.0 mg, 1.44 mmol) and anhydrous potassium carbonate (995.0 mg, 7.20 mmol) were successively added to the system. After addition, the system was purged with argon, and this operation was repeated ten times to ensure the inert gas atmosphere in the system. Then, the system was transferred in an oil bath at 90° C., heated and reacted overnight under stirring. After 4 h, the starting material disappeared by TLC detection. Heating was stopped, and the system was allowed to naturally cool to room temperature Ethyl acetate (20 mL) and water (20 mL) were added to the system and stirred vigorously, followed by standing for separation of layers. The aqueous phase was extracted with ethyl acetate (30 mL×3). The organic phase was combined, sequentially washed with water (20 mL*3) and saturated saline (20 mL), and dried over anhydrous sodium sulfate. The solution was concentrated under reduced pressure to remove the solvent and obtain the crude product, which was separated by column chromatography, to provide 3-bromo-5-chloro-4-((6-chloro-5-(propan-2-yl-1,1,1,3,3,3-hexadeutero)pyrazin-3-yl-4-deutero)oxy)aniline as off-white solid (3-1, 293.0 mg), with a yield of 53.0%. MS (ESI) m/z 383.0 [M+H]$^+$.

(2) Synthesis of 6-(4-amino-2-bromo-6-chlorophenoxy)-4-(propan-2-yl-1,1,1,3,3,3-hexadeutero)pyrazin-3(2H)-one-5-deuterium (3-2)

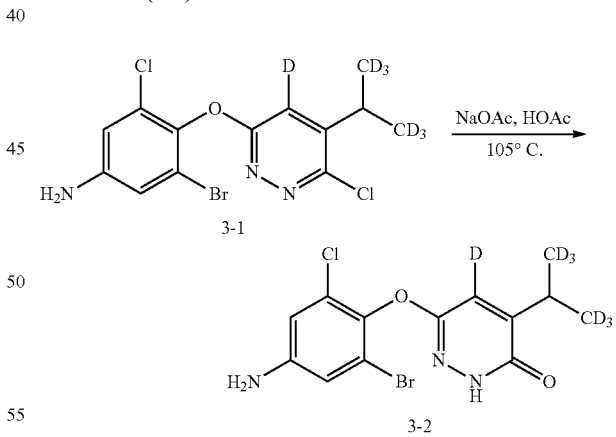

3-Bromo-5-chloro-4-((6-chloro-5-dideuteromethylmethyl-4-deuteropyridazine-3-yl)oxy)aniline (230.0 mg, 0.60 mmol) was weighed and placed in a 50 mL single-necked round bottom flask, to which was added glacial acetic acid (10 mL), and then the mixture was stirred at room temperature. Subsequently, anhydrous sodium acetate (172.0 mg, 2.10 mmol) was added to the system. After addition, the system was transferred in an oil bath at 105° C., and allowed to stir and react under reflux. After 22 h, the heating was stopped, and the system was naturally cooled to room temperature. The solvent was removed by rotatory evaporation, and water (50 mL) was added to the system, which was then transferred in an ice-water bath for cooling under stirring. When the internal temperature of the system was reduced to 5° C., sodium hydroxide solution (1.0 M) was added dropwise to the system, and pH value of the system was adjusted to be about 9. After that, ethyl acetate (50 mL) was added to the system, and then the solution was vigorously stirred, followed by standing for separation of layers. The aqueous phase was extracted with ethyl acetate (25 mL*2). The organic phase was combined, sequentially washed once with water (20 mL) and saturated saline (20 ML), and dried over anhydrous sodium sulfate. The solution was concentrated under reduced pressure to provide pale yellow solid. Methanol (10 mL) and NaOH solution (1.0 M, 10 mL) were sequentially added to a 100 mL three-necked round bottom flask containing the solid, and after addition, the system was transferred in an oil bath at 105° C. for reaction under reflux. After 11 h, heating was stopped, the oil bath was removed, and the system was warmed to room temperature. The solvent was removed by rotatory evaporation, and ethyl acetate (80 mL) and water (50 mL) were added to the residue. The resultant solution was vigorously stirred, and then allowed to stand for separation of layers. The aqueous layer was extracted with ethyl acetate (25 mL*2). The organic layer was combined, sequentially washed with water (20 mL*2) and saturated saline (20 mL), and dried over anhydrous sodium sulfate. The solvent was removed by rotatory evaporation to provide the crude product, which was separated by column chromatography to obtain 6-(4-amino-2-bromo-6-chlorophenoxy)-4-dideuteromethylmethyl-5-deuteropyridazine-3(2H)-one as pale yellow solid (3-2, 115.0 mg), with a yield of 52.5%. MS (ESI) m/z 365.1 [M+H]$^+$.

(3) Synthesis of compound ethyl (2-(2-(3-bromo-5-chloro-4-((6-oxo-5-(propan-2-yl-1,1,1,3,3,3-hexadeutero)-1,6-dihydropyrazin-3-yl-4-deutero)oxy)phenyl)hydrazono)-2-cyanoac etyl)carbamate (3-3)

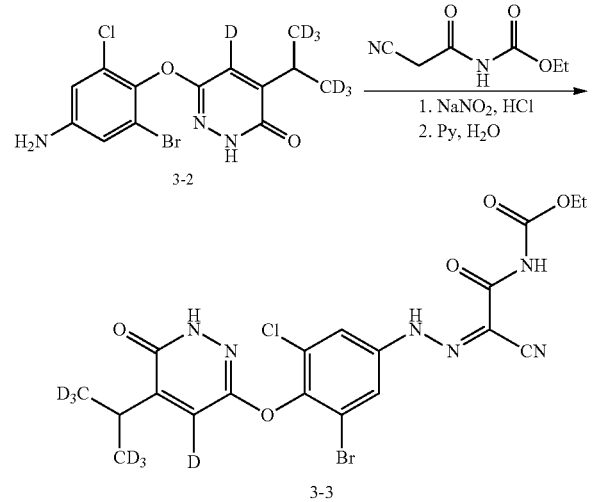

6-(4-Amino-2-bromo-6-chlorophenoxy)-4-dideuteromethylmethyl-5-deuteropyridazine-3(2H)-one (100.0 mg, 0.27 mmol) was weighed and placed in a 25 mL single-necked round bottom flask, to which was added water (3.7 mL), and the solution was stirred at room temperature. Subsequently, concentrated hydrochloric acid (1.9 mL) was added to the system. After addition, the system was transferred in an ice water bath for cooling under stirring. When the internal temperature of the system was reduced to 0° C., 0.5 mL aqueous solution of sodium nitrite (24.0 mg, 0.34 mmol was added dropwise to the system. After adding, the system was further stirred and reacted for 30 min at this temperature. In addition, N-cyanoacetylurea (47.0 mg, 0.30 mmol) was weighed and placed in a 50 mL single-necked round bottom flask, to which were successively added water (6.3 mL) and pyridine (1.9 mL). The resultant mixture was stirred at room temperature to obtain a clear solution, and then the system was transferred to an ice water bath for cooling under stirring for additional 30 min. The diazotizing reaction solution was added slowly to the system containing N-cyanoacetylurea, and the dropping rate was controlled so that the internal temperature of the system did not exceed 5° C. After addition, the system was allowed to stir and react in the ice water bath at this temperature. After 1 h, the reaction was completed by TLC detection. The system was filtered by suction, and the filter cake was rinsed several times with a small amount of water, washed several times with n-hexane, and dried to obtain ethyl (2-cyano-2-(2-(3-bromo-5-chloro-4-(5-dideuteromethylmethyl-4-deutero-6-oxo-1,6-dihydropyridazine-3-yl)oxy)phenyl)hydrazono)acetyl)carbamate (3-3, 104.0 mg), with a yield of 71.7%, which was directly used in the next step without further purification. MS (ESI) m/z 532.1 [M+H]$^+$.

(4) Synthesis of 2-(3-bromo-5-chloro-4-((4-deutero-5-(1,1,1,3,3,3-hexadeuteropropyl-2-yl)-6-oxo-1,6-dihydropyrazin-3-yl)oxy)phenyl)-3,5-dioxy-2,3,4,5-tetrahydro-1,2,4-triazine-6-nitrile (compound 3)

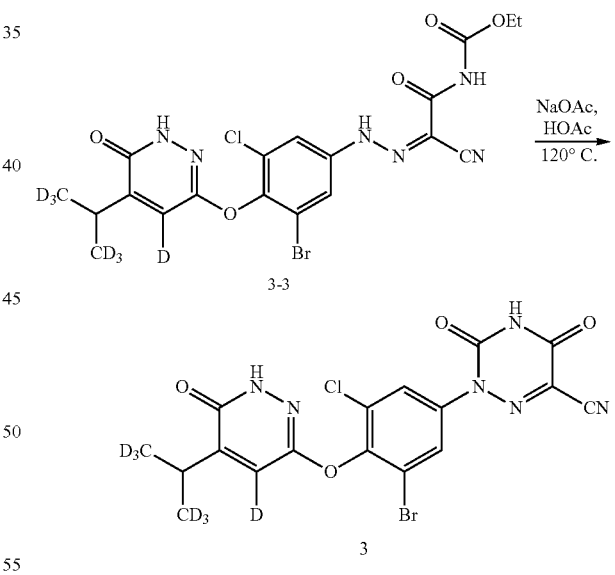

Etheyl (2-cyano-2-(2-(3-bromo-5-chloro-4-((5-dideuteromethylmethyl-4-deutero-6-oxo-1,6-dihydropyridazine-3-yl)oxy)phenyl)hydrazono)cyanoacetyl)carbamate (104.0 mg, 0.20 mmol) was weighed and placed in a 25 mL single-necked round bottom flask, to which was added glacial acetic acid (5 mL), and then the mixture was stirred at room temperature. Subsequently, anhydrous sodium acetate (82.0 mg, 1.00 mmol) was added to the system. After addition, the system was transferred in an oil bath at 120° C., and allowed to stir and react under heating. After 2 h, the starting material was completely consumed by TLC detection. The heating was stopped, and the system was naturally cooled to room temperature. The system was then transferred in an ice-water bath for cooling under stirring. When the internal temperature of the system was reduced to 5° C., to which was added ice water, and the resultant solution was vigorously stirred for 30 min. Then, the solution was filtered by suction, and the filter cake was rinsed with a small amount of water for several times, which was then dissolved in ethyl acetate, and dried over anhydrous sodium sulfate. The solvent was removed by rotatory evaporation to obtain a crude product, which was separated and purified by Pre-TLC to obtain 2-(3-bromo-5-chloro-4-((4-deutero-5-(1,1,1,3,3,3-hexadeuteropropyl-2-yl)-6-oxo-1,6-dihydropyrazin-3-yl)oxy)phenyl)-3,5-dioxy-2,3,4,5-tetrahydro-1,2,4-triazine-6-nitrile as light orange solid (compound 3, 68.0 mg), with a yield of 71.6%. MS (ESI) m/z 486.2 [M+H]$^+$. $^1$H NMR (400 MHz, DMSO-d$_6$) δ13.22 (s, 1H), 12.24 (s, 1H), 7.89 (d, J=4.0 Hz, 1H), 7.82 (d, J=4.0 Hz, 1H), 3.02 (s, 1H).

Example 3 Synthesis of 2-(3,5-dibromo-4-((6-oxo-5-(propan-2-yl-1,1,1,3,3,3-hexadeutero)-1,6-dihydropyrazin-3-yl)oxy)phenyl)-3,5-dioxo-2,3,4,5-tetrahydro-1,2,4-triazine-6-nitrile (compound 14)

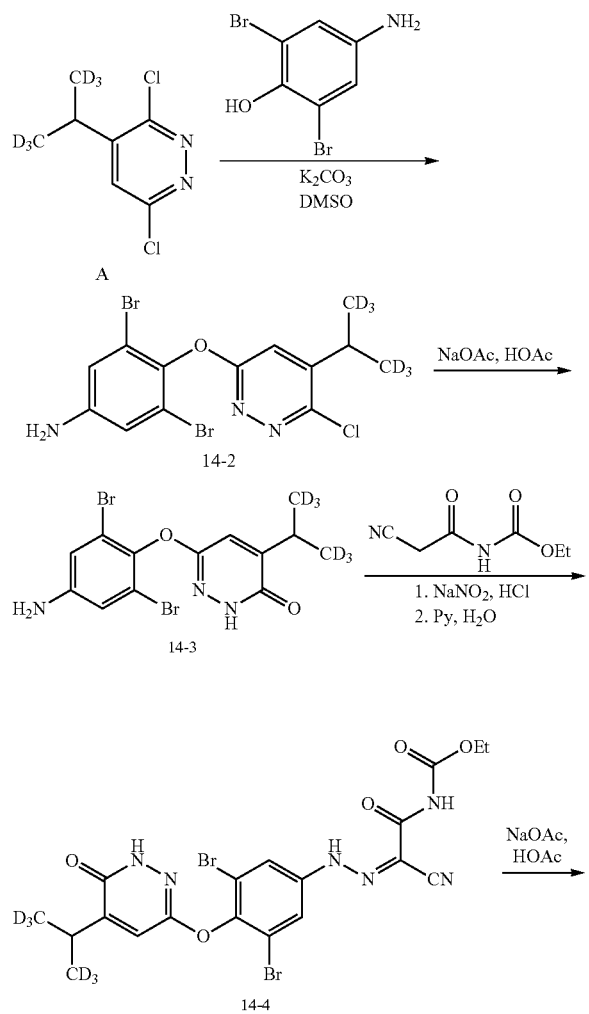

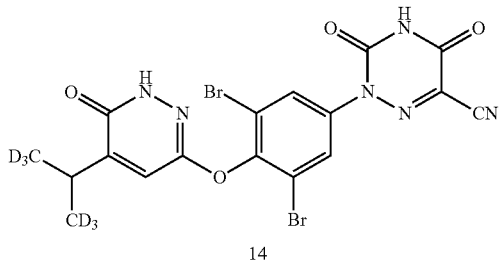

(1) Synthesis of 3,5-dibromo-4-((6-chloro-5-(propan-2-yl-1,1,1,3,3,3-hexadeutero) pyridazin-3-yl)oxy)aniline:

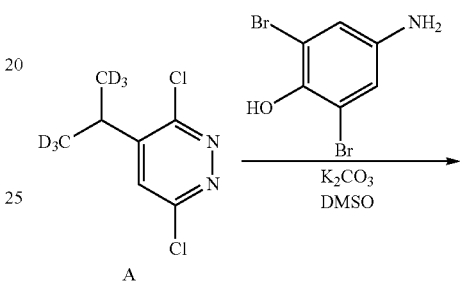

Compound 3,6-dichloro-4-(propan-2-yl-1,1,1,3,3,3-hexadeutero)pyridazine A (330 mg, 1.67 mmol) was dissolved in 5 ml of DMSO, to which was added compound 4-amino-2,6-dibromophenol (559 mg, 2.09 mmol), and then K$_2$CO$_3$ (923 mg, 6.68 mmol) was added to the system under stirring. The system was purged with Ar for three times, and then heated to 90° C. and allowed to react for 3 h. Then, the system was cooled, to which was added water, and the resultant solution was extracted with ethyl acetate. The organic layer was sequentially washed with water and saturated saline, dried over anhydrous sodium sulfate, and then concentrated under reduced pressure to dry. The residue was separated and purified by column chromatography (petroleum ether/ethyl acetate=5:1), to provide compound 3,5-dibromo-4-((6-chloro-5-(propan-2-yl-1,1,1,3,3,3-d$_6$)pyridazin-3-yl)oxy)aniline (14-2, 210 mg), with a yield of 30%, MS (ESI) m/z 426.0.0 [M+H]$^+$.

(2) Synthesis of 6-(4-amino-2,6-dibromophenoxy)-4-(propan-2-yl-1,1,1,3,3,3-d$_6$)pyridazine-3(2H)-one

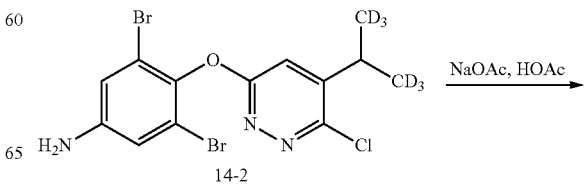

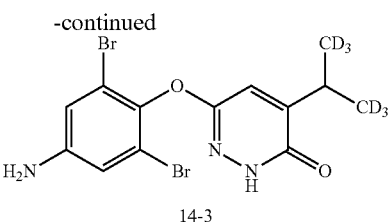

Compound 3,5-dibromo-4-((6-chloro-5-(propan-2-yl-1,1,1,3,3,3-d₆)pyridazin-3-yl)oxy)aniline (185 mg, 0.43 mmol) was dissolved in 5 ml of acetic acid, to which was added anhydrous sodium acetate (142 mg, 1.7 mmol) under stirring. The mixture was allowed to react overnight at 105° C., and then cooled to room temperature. The resultant solution was concentrated under reduced pressure to dry, and pH value of the residue was adjusted to be 9 with 6 N of NaOH solution. The solution was extracted with 20 ml of ethyl acetate, and the water layer was further extracted once with 15 ml of ethyl acetate. The organic layer was combined, sequentially washed with water and saturated saline, dried over anhydrous sodium sulfate, and then concentrated under reduced pressure to dry. 10 ml of methanol was added to the residue, to which was added 10 ml of 1N NaOH aqueous solution, and the mixture was allowed to react overnight at 105° C. The reaction solution was cooled, and then most of methanol was evaporated under reduced pressure, to which was added 20 ml of ethyl acetate. The organic layer was sequentially washed with water and saturated saline, dried over anhydrous sodium sulfate, and then concentrated under reduced pressure to dry. The residue was separated and purified by column chromatography (petroleum ether/ethyl acetate=3:2), to provide compound 6-(4-amino-2,6-dibromophenoxy)-4-(propan-2-yl-1,1,1,3,3,3-d₆)pyridazin-3(2H)-one (14-3, 130 mg), with a yield of 73.9%, MS (ESI) m/z 408.0 [M+H]⁺.

(3) Synthesis of ethyl-(2-cyano-2-(2-(3,5-dibromo-4-((6-oxo-5-(propan-2-yl-1,1,1,3,3,3-d₆)-1,6-dihydropyridazine-3-yl-4-d)oxy)phenyl)hydrazono)ethyl)carbamate

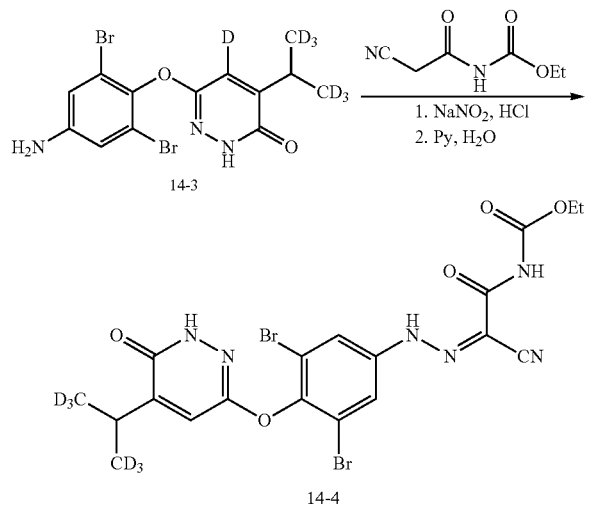

Compound 6-(4-amino-2,6-dibromophenoxy)-4-(propan-2-yl-1,1,1,3,3,3-d₆) pyridazine-3(2H)-one (125 mg, 0.31 mmol) was added to a round-bottomed flask, to which were successively added 4.6 ml of water and 2.2 ml of concentrated hydrochloric acid, and then the system was transferred to an ice-water bath and kept for 30 min. N-cyanoacetylurethane (52 mg, 0.33 mmol) was added to a round-bottomed flask, to which were successively added 8 ml of water and 2.2 ml of pyridine, and then the system was moved to an ice-water bath and kept for 30 min. The reaction solution obtained in the previous step was added to the reaction system. After addition, the system was kept at this temperature and stirred for 30 min. The resultant solution was filtered, and the filter cake was rinsed with 30 ml of water and dried to obtain the product ethyl-(2-cyano-2-(2-(3,5-dibromo-4-((6-oxo-5-(propan-2-yl-1,1,1,3,3,3-d₆)-1,6-dihydropyridazine-3-yl-4-d)oxy)phenyl)hydrazono)ethyl)carbamate as purple-red solid (14-4, 130 mg), with a yield of 72.8%, MS (ESI) m/z 576.1 [M+H]⁺.

(4) Synthesis of 2-(3,5-dibromo-4-((6-oxo-5-(propan-2-yl-1,1,1,3,3,3-d₆)-1,6-dihydropyridazine-3-yl)oxy)phenyl)-3,5-dioxo-2,3,4,5-tetrahydro-1,2,4-triazine-6-formonitrile

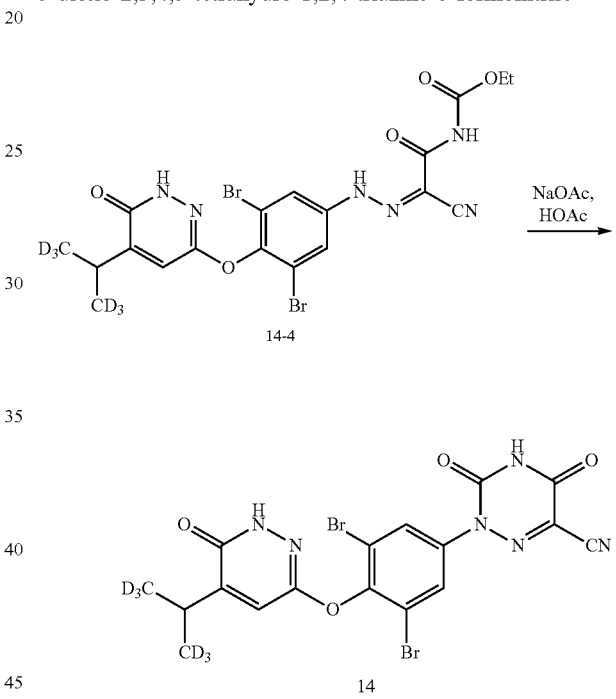

Compound ethyl-(2-cyano-2-(2-(3,5-dibromo-4-((6-oxo-5-(propan-2-yl-1,1,1,3,3,3-d₆)-1,6-dihydropyridazine-3-yl-4-d)oxy)phenyl)hydrazono)ethyl)carbamate (125 mg, 0.22 mmol) was dissolved in 5 ml of acetic acid, to which was added sodium acetate (73 mg, 0.88 mmol), and the reaction solution was refluxed at 125° C. for 2 h. Then, the solution was cooled in an ice water bath, to which was added 30 ml of water, and then stirred for 20 min. The resultant solution was filtered, and the filter cake was rinsed with water for three times and dried. The obtained solid was added into 3 ml of ethyl acetate and beaten for 30 min. The solution was filtered, and the filter cake was concentrated under reduced pressure to dry, to obtain compound 2-(3,5-dibromo-4-((6-oxo-5-(propan-2-yl-1,1,1,3,3,3-d₆)-1,6-dihydropyridazine-3-yl)oxy)phenyl)-3,5-dioxo-2,3,4,5-tetrahydro-1,2,4-triazine-6-formonitrile (compound 14, 95 mg), with a yield of 81.4%, MS (ESI) m/z 529.0 [M+H]⁺. ¹H NMR (400 MHz, DMSO-d₆) δ13.44-13.12 (m, 1H), 12.23 (s, 1H), 7.92 (s, 2H), 7.44 (s, 1H), 3.02 (s, 1H).

Example 4 Synthesis of Compound 1

Compound 2-(3-bronco-5-chloro-4-((5-isopropyl-6-oxo-1,6-dihydropyridazin-3-yl)oxy)phenyl)-3,5-dioxo-2,3,4,5-tetrahydro-1,2,4-triazine-6-nitrile (compound 1)

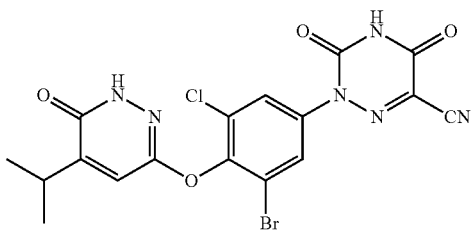 [SMILES: CC(C)c1cc(Oc2c(Cl)cc(-n3nc(C#N)c(=O)[nH]c3=O)cc2Br)n[nH]c1=O]

Using known compound 3,6-dichloro-4-isopropylpiperazine (PCT Int. Appl., 2013045519) as starting material, compound 1 was prepared by reference to the method of Example 1.

LC/MS (ESI$^+$) calcd for $C_{17}H_{12}BrClN_6O_4$ [M+H]$^+$ m/z, 477.98; found, 479.0, 481.0. $^1$NMR (400 MHz, DMSO-d$_6$) δ13.29 (s, 1H), 12.22 (s, 1H), 7.88 (d, J=2.4 Hz, 1H), 7.81 (d, J=2.4 Hz, 1H), 7.44 (s, 1H), 3.05 (dt, J=13.8, 6.9 Hz, 1H), 1.20 (d, J=6.9 Hz, 6H).

Example 5 Synthesis of Compound 13

2-(3,5-Dibromo-4-((5-isopropyl-6-oxo-1,6-dihydropyridazin-3-yl)oxy)phenyl)-3,5-dioxy-2,3,4,5-tetrahydro-1,2,4-triazine-6-nitrile (compound 13)

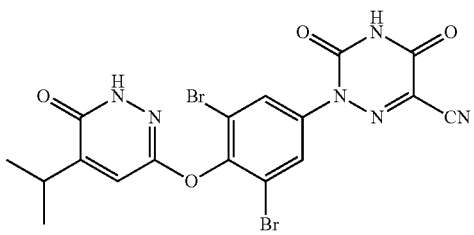 [SMILES: CC(C)c1cc(Oc2c(Br)cc(-n3nc(C#N)c(=O)[nH]c3=O)cc2Br)n[nH]c1=O]

Using known compound 3,6-dichloro-4-isopropylpiperazine (PCT Int. Appl., 2013045519) as starting material, compound 13 was prepared by reference to the method of Example 3, LC/MS (ESI$^+$) calcd for $C_{17}H_{12}Br_2N_6O_4$ [M+H]$^+$ m/z, 524.13; found, 523.1, 525.1. $^1$H NMR (400 MHz, DMSO-d$_6$) δ12.16 (s, 1H), 7.91 (s, 2H), 7.42 (s, 1H), 3.06 (dt, J=13.7, 6.9 Hz, 1H), 1.20 (d, J=6.8 Hz, 6H).

Example 6 Synthesis of Compound 15

2-(3,5-dibromo-4-((6-oxo-5-(propan-2-yl-1,1,1,3,3,3-d$_6$)-1,6-dihydropyridazin-3-yl-4-d)oxy)phenyl)-3,5-dioxy-2,3,4,5-tetrahydro-1,2,4-triazine-6-nitrile (compound 15)

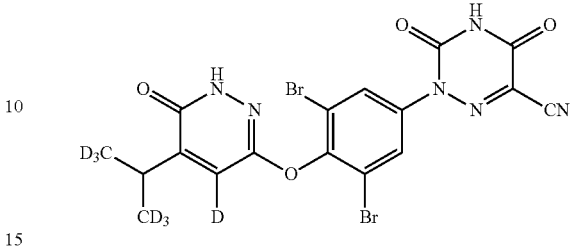

Using above compound B as starting material, compound 15 was prepared by reference to the method of Example 3.

LC/MS (ESI$^+$) calcd for $C_{17}H_5D_7Br_2N_6O_4$ [M+H]$^+$ m/z 531.17; found, 530.0, 532.0, $^1$H NMR (400 MHz, DMSO-d$_6$) δ13.28 (s, 1H), 12.23 (s, 1H), 7.92 (s, 2H), 3.02 (s, 1H).

The beneficial effects of the present invention were demonstrated by the following Experimental examples.

Experimental Example 1 Experiment on the Agonistic Activity of the Compound According to the Present Invention on THR-β

1) Experimental Method

The agonistic activity of the compound on THR-β was tested by a method similar to the literature (*J. Med. Chem.* 2014, 57, 3912):

100× solutions of reference compounds or compounds were prepared with DMSO and then diluted in a 1:3 equal ratio. The gradient dilution of 100× reference compound or compound was further diluted to 4× with 1× reaction buffer and then added to the test plate. A mixed solution of 4× TRα-LBD or TRβ-LBD and 4× RXRα was prepared with 1× reaction buffer and added to the test plate. A mixed solution of 2× biotin-SRC2-2,2× Eu-anti-GST and 2× streptavidin-d2 was prepared with 1× reaction buffer and added to the test plate. The plate was centrifuged at 1000 rpm for 1 min and then incubated at room temperature and in the dark for 4 h. The fluorescence signal intensity at 665 nm and 615 nm was read on EnVision 2104 plate reader, and Ratio$_{665\ nm/615\ nm}$ was calculated to obtain the THR-β EC$_{50}$ value (nM) for THR-β.

The agonistic activity of the compound of the present invention on the thyroid hormone receptor α (THR-α) was tested by the above-mentioned similar method, and for THR-α, the THR-α EC$_{50}$ value (nM) was calculated, which was used to calculate the agonistic selectivity of the compound of the present invention on THR-β/THR-α.

Selectivity THR-β/THR-α=THR-αEC$_{50}$÷THR-β EC$_{50}$.

2) Experimental Results

TABLE 1

The agonistic activity and selectivity of the compounds of the present invention for THR-β and THR-α.

| Compounds | THR-β EC$_{50}$ (nM) | THR-α EC$_{50}$ (nM) | Selectivity THR-β/THR-α |
|---|---|---|---|
| MGL-3196 | 168 | 1720 | 10 |
| 1 | 57 | 1017 | 18 |
| 2 | 52 | 1061 | 20 |

TABLE 1-continued

The agonistic activity and selectivity of the compounds of the present invention for THR-β and THR-α.

| Compounds | THR-β EC$_{50}$ (nM) | THR-α EC$_{50}$ (nM) | Selectivity THR-β/THR-α |
|---|---|---|---|
| 3 | 60 | 1331 | 22 |
| 13 | 30 | 800 | 27 |
| 14 | 27 | 326 | 12 |
| 15 | 19 | 349 | 18 |

The results are shown in Table 1. It could be seen that compounds 1, 3, 13, 14, and 15 of the present invention had significantly higher agonistic activities for both THR-β and THR-α as compared to the control compound MGL-3196, and in particular for THR-β, the compounds of the present invention had significantly higher agonistic activities. In addition, as for THR-β and THR-α, the compounds of the present invention also had significantly higher agonistic selectivity for THR-β as compared to the control compound MGL-3196.

Experimental Example 2 Pharmacokinetic Tests of Compounds of the Present Invention in Mice 1) Experimental Materials and Instruments:
Polyethylene glycol 400 (PEG400), manufacturer: Chengdu Kelong Chemical Reagent Factory;
Hydroxypropyl 3-cyclodextrin (HP-β-CD), manufacturer: Shanghai Dibai Chemical Technology Co., Ltd.;
HPC LF, manufacturer: Chengdu Yuannuo Tiancheng Technology Co., Ltd.;
Heparin sodium, manufacturer: Chengdu Kelong Chemical Reagent Factory.
Experimental animals: ICR mice (Chengdu Dossy Experimental Animals CO., LTD.)

2) Experimental Method
Preparation of Test Compound Solution
IV group: 1.15 mg of test compound was accurately weighed, and then DMA (0.228 ml) was added to dissolve the compound, to which were successively added PEG400 (1.139 ml) and 0.1 M of phosphate buffer (5.012 ml). Finally, 40% HP-B-CD was added to the final volume of 11.39 ml. The solution was thoroughly mixed by ultrasonic vortex. A clear solution at the concentration of 0.1 mg/ml was prepared.
PO group: 5.06 mg of test compound was precisely weighed, and then 2% HPC LF (containing 0.1% Tween-80) was added to the final volume of 20.04 ml. The solution was mixed by ultrasound, to prepare a uniform suspension at the concentration of 0.25 mg/ml.

Experimental Procedures:
After fasting overnight (free drinking water), nine adult ICR mice (3 mice for each time point) were administered by injection via tail vein and by gavage, respectively. For IV group, 5 min, 15 min, 0.5 h, 1 h, 2 h, 4 h, 8 h, 12 h and 24 h after administration, 0.1 ml of blood was collected from the submandibular vein, centrifuged at 4° C. for 5 min to separate the plasma, and stored at −20° C. for detection. For PO group, before administration and 0.5 h, 1 h, 2 h, 4 h, 6 h, 8 h, 12 h and 24 h after administration, 0.1 ml of blood was collected from the submandibular vein, and the processing was the same as that of IV group.

Then, the concentration of original drug in plasma was determined by LC/MS/MS. The plasma concentration-time curve was plotted, and the main pharmacokinetic parameters were calculated with WinNonlin 6.3 software (see Table 2).

3) Experimental Results

TABLE 2

Pharmacokinetic experiments in mice.

| Compound | Dosage | Peak time T$_{max}$ (h) | Peak concentration C$_{max}$ (□g/mL) | Exposure AUC$_{inf}$ (□g*h/mL) | Half-life T$_{1/2}$ (h) |
|---|---|---|---|---|---|
| MGL-3196 | 5 mg/kg | 2 | 1.37 | 9.36 | 2.81 |
| Compound 2 | 2 mg/kg | 4 | 0.96 | 9.26 | 5.25 |

As could be seen from Table 2, the compound of the present invention was exposed to a dose of 5 mg/kg in mice when MGL-3196 was administrated at a dose of 2 mg/kg; and compound 2 of the present invention at a lower dose had a longer halts-life than MGL-3196. It was demonstrated that the compounds of the present invention had better pharmacokinetic properties than MGL-3196.

In summary, the present invention provided a compound of formula (I) or an optical isomer, a salt, a prodrug, a hydrate or a non-aqueous solvate thereof. Compared with the control compound MGL-3196, the compound of formula (I), which is obtained by specific substitution sites and specific substitution types in the present invention, displayed a higher agonistic activity on both THR-β and THR-α, and especially for THR-β, the compound of the present invention had a significantly improved agonistic activity and selectivity. In addition, the compound of the present invention also demonstrated a significantly improved pharmacokinetic properties, and had a good application prospect in the preparation of THR-β agonists and drugs for the treatment of THR-β agonist indications (including dyslipidemia, hypercholesteremia, non-alcoholic steatohepatitis and non-alcoholic fatty liver disease)

The invention claimed is:

1. The compound represented by formula (I), or an optical isomer thereof, or a salt thereof:

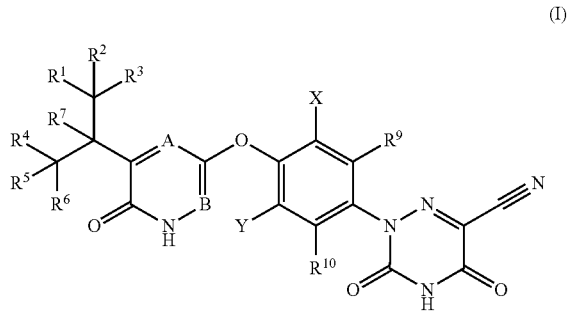

(I)

wherein, each of $R^1$-$R^7$, $R^9$, and $R^{10}$ is independently selected from H and D; A is selected from the group consisting of CH and CD; B is N; X and Y are each independently selected from the group consisting of Cl and Br; X and Y are not Cl at the same time.

2. The compound according to claim 1 or an optical isomer, a salt thereof, characterized in that said compound has the structure of formula (II):

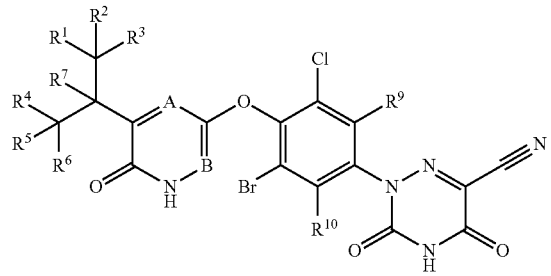

(II)

wherein, each of R¹-R⁷, R⁹, and R¹⁰ is independently selected from H and D; A is selected from the group consisting of CH and CD; B is N.

3. The compound according to claim 2, or an optical isomer thereof, or a salt thereof, characterized in that said compound has the structure of formula (IV):

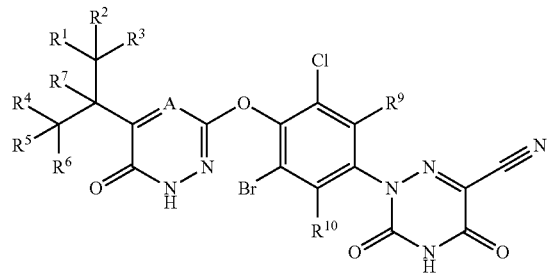

(IV)

wherein, R⁷, R⁹, and R¹⁰ are each independently selected from H; each of R¹-R⁶ is independently selected from H and D; A is selected from CH and CD.

4. The compound according to claim 1, or an optical isomer thereof, or a salt thereof, characterized in that said compound has the structure of formula (III):

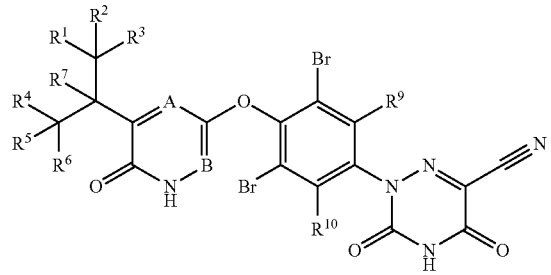

(III)

wherein, each of R¹-R⁷, R⁹, and R¹⁰ is independently selected from H and D; A is selected from the group consisting of CH and CD; B is N.

5. The compound according to claim 4, or an optical isomer thereof, or a salt thereof, characterized in that said compound has the structure of formula (V):

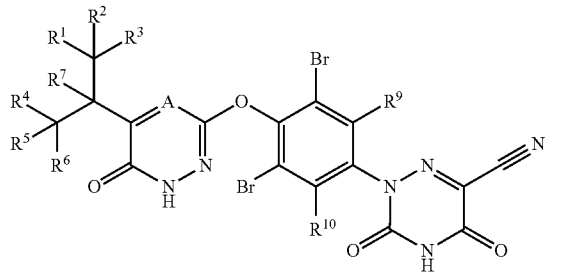

(V)

wherein, R⁷, R⁹, and R¹⁰ are each independently selected from H; each of R¹-R⁶ is independently selected from H and D; A is selected from CH and CD.

6. The compound according to claim 1, or an optical isomer thereof, or a salt thereof, characterized in that said compound is selected from the group consisting of the following compounds:

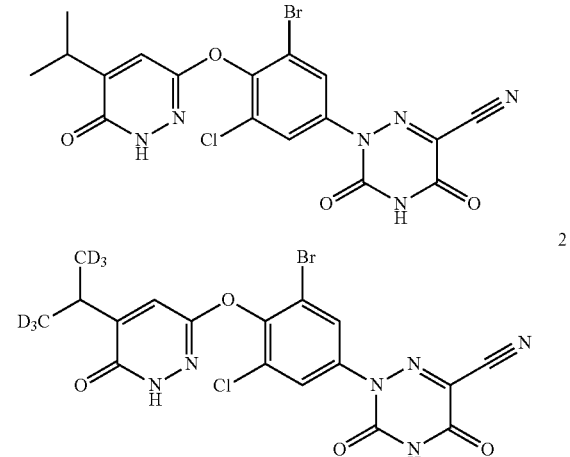

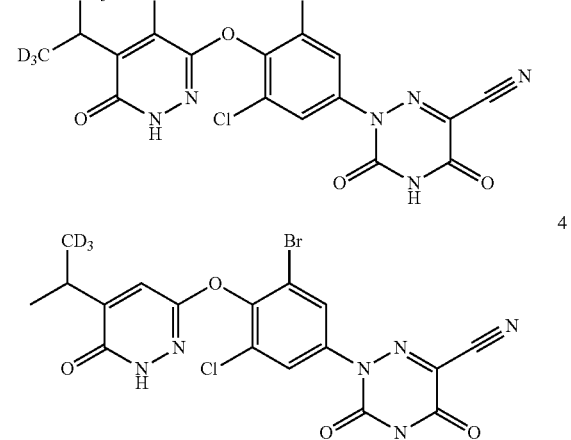

35
-continued
5
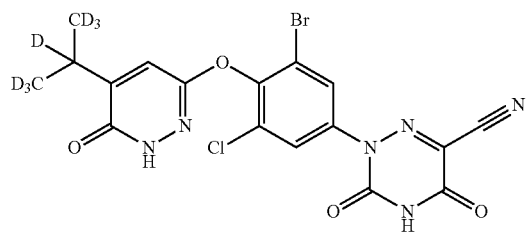
6
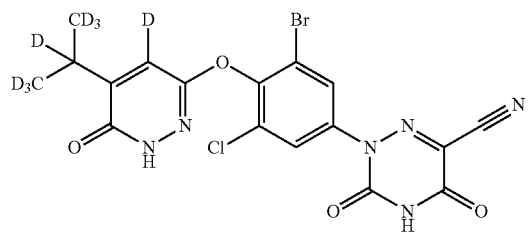
7
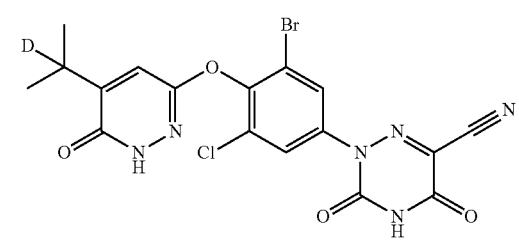
8
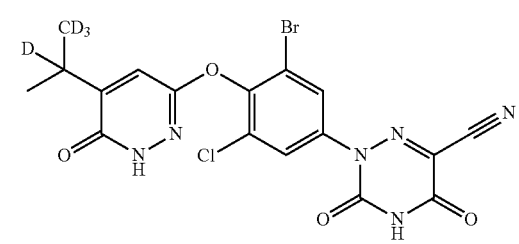
9
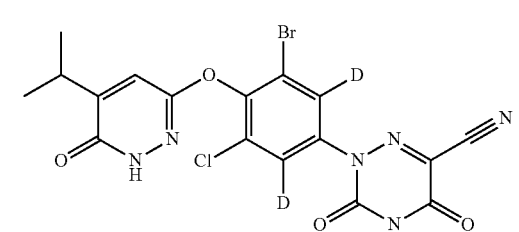
10
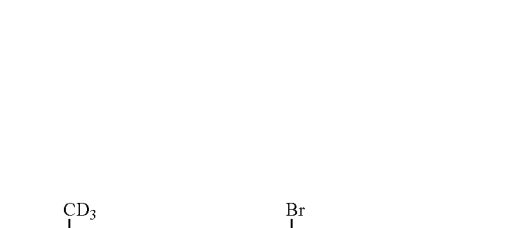
36
-continued
11
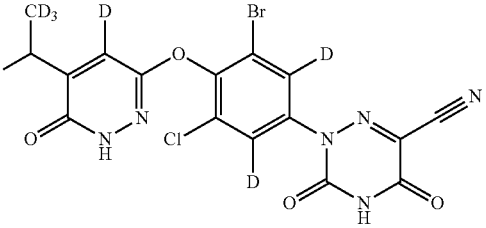
12
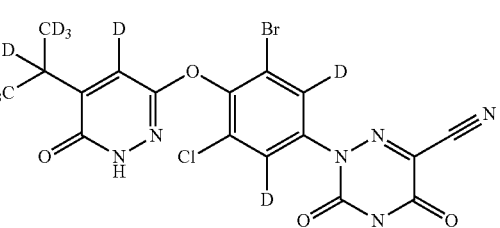
13
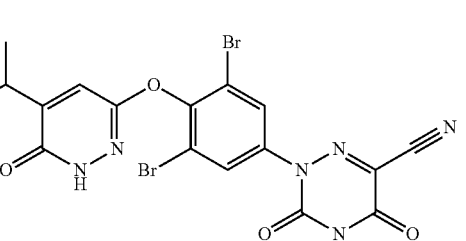
14
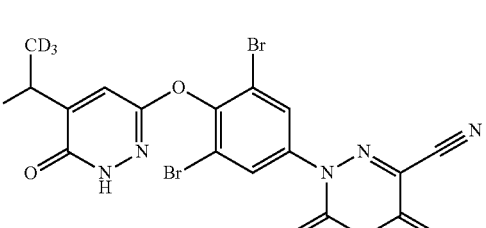
15
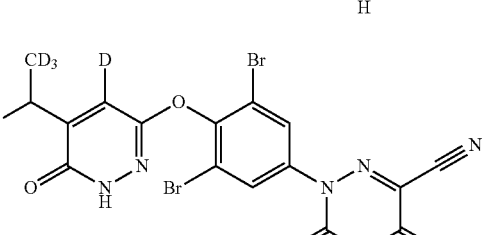
16
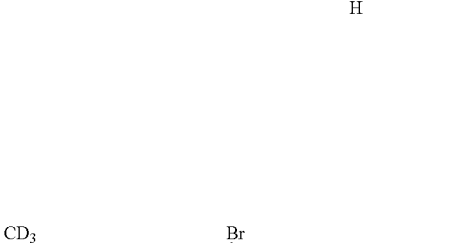

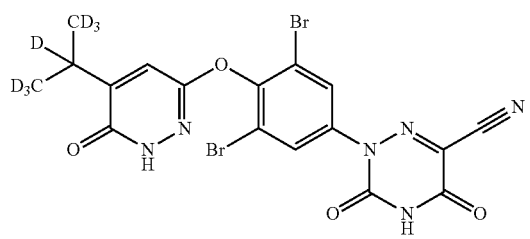

17

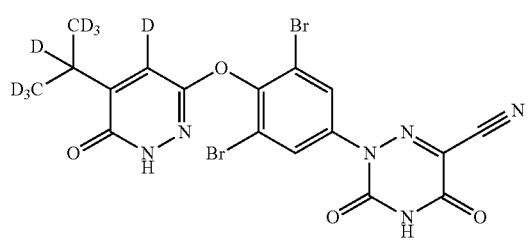

18

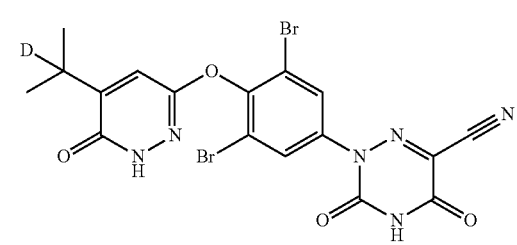

19

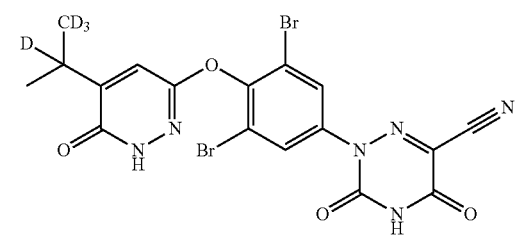

20

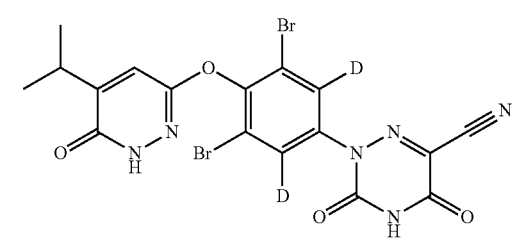

21

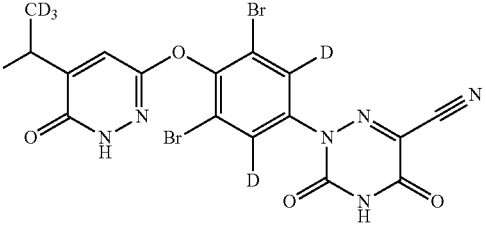

22

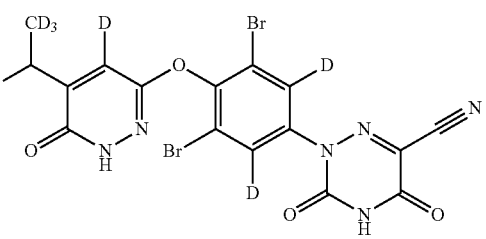

23-1

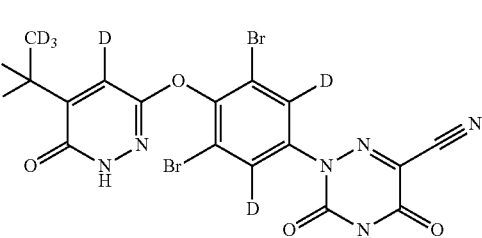

23-2

7. A medicament for lowering cholesterol and treating dyslipidemia and nonalcoholic fatty liver disease, characterized by which it is a formulated drug product containing an active ingredient that is the compound according to claim 1, or an optical isomer, or a salt thereof, and pharmaceutically acceptable auxiliary materials and excipients.

8. A method of activating THR-β receptors, comprising administering an effective amount of a composition that contains the compound according to claim 1, or an optical isomer, or a salt thereof to a subject in need thereof.

9. A method of treating diffuse toxic goiter, comprising administering an effective amount of a THR-α agonist to a subject in need thereof, wherein the THR-α agonist is the compound according to claim 1, or an optical isomer thereof, or a salt thereof.

10. The method of claim 8, wherein the composition is a drug for lowering cholesterol, and treating dyslipidemia and nonalcoholic fatty liver disease.

11. The method of claim 8, wherein the composition is a drug for the treatment of familial hypercholesterolemia and non-alcoholic steatohepatitis.

* * * * *